US007001609B1

(12) United States Patent
Matson et al.

(10) Patent No.: US 7,001,609 B1
(45) Date of Patent: Feb. 21, 2006

(54) MUCOSAL ORIGINATED DRUG DELIVERY SYSTEMS AND ANIMAL APPLICATIONS

(75) Inventors: Charles J. Matson, Stillwater, MN (US); Yen-Lane Chen, New Brighton, MN (US); Daniel T. Ruth, Mahtomedia, MN (US); Luce R. M. Benes, Orleans (FR); Sophie G. Burgaud, Angers (FR); Francoise L. R. Horriere, Angerville (FR); Isabelle M. L. Seyler, Pithiviers (FR)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/806,086

(22) PCT Filed: Oct. 1, 1999

(86) PCT No.: PCT/US99/22967

§ 371 (c)(1),
(2), (4) Date: Jun. 22, 2001

(87) PCT Pub. No.: WO00/19987

PCT Pub. Date: Apr. 13, 2000

Related U.S. Application Data

(60) Provisional application No. 60/102,956, filed on Oct. 2, 1998.

(51) Int. Cl.
*A61F 13/02* (2006.01)
*A61F 9/02* (2006.01)
(52) U.S. Cl. ..................... 424/434; 424/435; 424/436
(58) Field of Classification Search ............... 424/434, 424/435, 448, 489, 436; 514/953; 423/434, 423/435, 436
See application file for complete search history.

(56) References Cited

U.S. PATENT DOCUMENTS

| 3,699,963 | A | | 10/1972 | Zaffaroni |
| 3,972,995 | A | | 8/1976 | Tsuk et al. |
| 4,876,092 | A | | 10/1989 | Mizobuchi et al. |
| 4,900,552 | A | | 2/1990 | Sanvordeker et al. |
| 5,113,860 | A | | 5/1992 | McQuinn |
| 5,346,701 | A | | 9/1994 | Heiber et al. |
| 5,527,610 | A | * | 6/1996 | Urry .......................... 428/373 |
| 5,578,315 | A | | 11/1996 | Chien et al. |
| 5,639,469 | A | * | 6/1997 | Benes et al. ................. 424/435 |
| 5,656,286 | A | | 8/1997 | Miranda et al. |
| 5,688,520 | A | | 11/1997 | Karsenty et al. |
| 5,723,143 | A | | 3/1998 | Jacques et al. |

(Continued)

FOREIGN PATENT DOCUMENTS

GB          981 372 A      1/1965

(Continued)

OTHER PUBLICATIONS

Stenberg D., "Physiological Role of $\alpha_2$-adrenoceptors in the Regulation of Vigilance and Pain: Effect of Medetomidine," *Acta Vet. Scand.*, 85:21-28 (1989).
Hamline Robert L. et al., "Studies to Determine the Optimal Dose of Medetomidine," *Acta Vet. Scand.*, 85:89-95 (1989).

(Continued)

*Primary Examiner*—Carlos A. Azpuru
(74) *Attorney, Agent, or Firm*—Mueting Raasch & Gebhardt, P.A.

(57) ABSTRACT

The present invention is directed to mucosal originated drug delivery systems and methods for using the drug delivery system to treat conditions in animals. Conditions amenable to treatment according to the invention are also described. The described mucosal drug delivery systems provide for drug release across a mucosal membrane as well as release away from the mucosal membrane.

9 Claims, 16 Drawing Sheets

U.S. PATENT DOCUMENTS 5,750,134 A    5/1998   Scholz et al.
5,750,136 A *  5/1998   Scholz et al. ............... 424/448
5,780,045 A    7/1998   McQuinn et al.

FOREIGN PATENT DOCUMENTS

GB           1541609 A    3/1979

OTHER PUBLICATIONS

Jöchle, W. et al., "Sedation and Analgesic with DOMOSEDAN® (Detomidine HCl) in Horses: Dose Response Studies on Efficacy and its Duration," *Acta Vet. Scand.*, 82:69-84 (1986).

* cited by examiner

MUCOSAL ORIGINATED DRUG DELIVERY SYSTEMS AND ANIMAL APPLICATIONS

This application claims benefit of Provisional Application Ser. No. 60/102,956 filed Oct. 2, 1998.

FIELD OF THE INVENTION

The present invention is directed to mucosal bioadhesive systems and methods of use. Specifically, the invention provides mucosal originated drug delivery systems for local or systemic drug delivery. The systems disclosed are particularly advantageous for use in animals.

BACKGROUND OF THE INVENTION

Similarities in physiological functions between humans and some non-human animals are well known. These similarities permit numerous pharmacological agents to provide therapeutic or diagnostic efficacy across species lines. Advantageously, the ability for a pharmacological agent to cross over species lines provides for therapeutic efficacy of new animal drugs in humans and new human drugs in animals.

However, the interspecies efficacy of a pharmacological agent can often be limited by certain fundamental differences which exist between humans and animals as well as between different animals. For example, interspecies differences at the cellular level for uptake, distribution, metabolism or elimination of a pharmacological agent can cause variability in the efficacy, toxicity or side effects of equivalent dosages administered to different animals or a human. In addition, differences in anatomy, size, disposition, availability of an accessible or safe administration route or reasoning capability often limits cross species utility. Moreover, housing conditions, frequency of administration or the skill level of the animal handler can limit practical utility of some agents across species lines. Thus, although physiological similarities exist between humans and non-human animals, these similarities are only one factor in the successful therapeutic effect of a pharmacological agent across species lines.

Safety, convenience, cost and skill level of the treatment provider are some of the factors affecting successful pharmacological treatment of conditions in animals. Often times animals are under the direct care of owners, trainers, or other handlers that lack expertise in administering a pharmacological agent to the animal. The general lack of second party payment systems for animal health care can make routine visits by a veterinarian (or other skilled animal care provider), or prolonged hospitalization, cost prohibitive to the owner. In addition, the fractious nature of some animals can preclude safe drug administration to the animal even by skilled handlers. Moreover, in rural areas, emergency situations frequently necessitate therapeutic action sooner than a veterinarian can arrive to provide the necessary treatment. Because of these and other factors unique to providing health care to animals, physiological similarity is only one factor affecting the therapeutic benefit of a pharmacological agent across species lines.

Typically, drugs are administered to animals orally or parenterally. And, while some pharmacological agents are available in an oral dosage form, to ensure that the necessary dose is administered, many agents must be administered by injection or directly to the stomach using a stomach tube. These administration methods can ensure proper dose administration, however, repeated administration via injection or stomach tube can quickly become irritating and stressful to the animal as well as dangerous to the animal owner or health care provider.

GB-A-981 372 describes a solid formulation suitable for oral administration to animals, being in the form of wafers readily adherent to the tongue or buccal mucosa and comprising a physiologically active substance, a solid non-toxic adhesive, a non-toxic humectant and a plasticizer.

EP-A-0 654 261 relates to a solid mucoadhesive therapeutic or hygienic composition, for human or veterinary use, intended to be administered by application to the buccal or nasal mucous membrane, this composition comprising, in mixture, a cellulosic ether gelifiable in the presence of an aqueous liquid, a homopolymer or copolymer of acrylic acid or a physiologically acceptable salt of that homopolymer or copolymer, and at least one therapeutic or hygienic active constituent.

WO-A-94/18925 describes a system for mucosally administering a macromolecular drug to the oral cavity comprising an inner drug/enhancer/polymer layer having one surface adapted to contact the mucosal tissue of the oral cavity and adhere thereto when wet and an opposing surface in contact with and adhering to an overlying inert layer, said inner layer containing from about 2 to 60 wt.-% of a bile salt enhancer, 5 to 65 wt.-% of a hydrophilic polymer and an effective amount of a macromolecular drug having a molecular weight of at least 500 daltons.

Hence, there is a need for effective diagnostic and therapeutic products and methods for animals that are humane, cost effective, easy to administer, and safe for both the animal and the health care provider.

SUMMARY OF THE INVENTION

The present disclosure is directed to new products and methods for safe, simple, effective, and humane treatment or diagnosis of a condition in animals. It will be appreciated, however, that many of the procedures disclosed herein can also be used advantageously for some human patients or conditions.

In several places throughout the specification, guidance is provided through lists of examples. In each instance, the recited list serves only as a representative group. It is not meant, however, that the list is exclusive.

The present invention provides safe and convenient drug delivery for short term or prolonged drug administration to a patient. The invention includes use of mucosal originated drug delivery systems. Included within mucosal originated drug delivery systems of the invention are known transmucosal drug delivery (TMDD) systems as well as new TMDD compositions. Mucosal originated drug delivery systems also include devices which release a drug away from the mucosal surface into the environment surrounding the delivery system. The invention also provides preferred water-insoluble polymer matrices for a delivery device that is particularly advantageous for adhering to moist mucosal membranes while releasing drug from the matrix in a controlled fashion.

DETAILED DESCRIPTION OF THE PREFERRED EMBODIMENT

Figure 1:
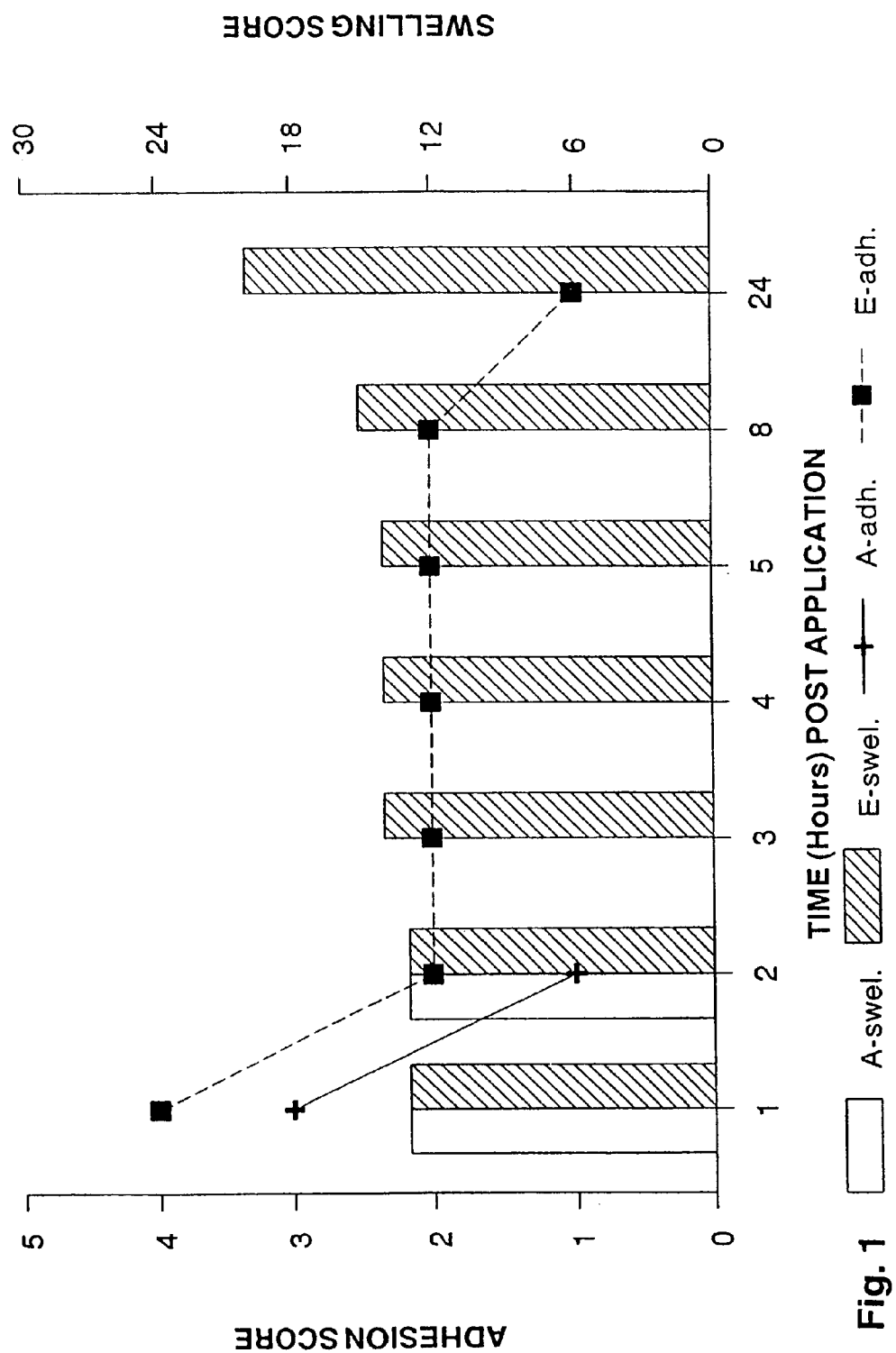
FIG. 1 is a graph illustrating adhesion and swelling scores of one embodiment of a transmucosal drug delivery system adhered to the buccal mucosa in canines.

As discussed above, in many instances, therapeutic agents which are physiologically acceptable across species lines are ineffective for use in a particular animal or animal specie due to unavailability of an effective dosage form, need for frequent readministration, size or anatomical hindrance to an effective administration route, unavailability of humane restraint mechanisms for administration, fractious disposition of the animal, inadequate housing facilities, unskilled personnel, etc. The present invention provides the animal care provider with novel, safe and humane methods for addressing practical problems of drug administration that are unique to animal husbandry methods.

The invention is directed to mucosal originated drug delivery systems and methods of use. As used herein, "mucosal originated drug delivery systems" are adhered to a mucous membrane and provide a source of a drug at the membrane. Thus, the drug delivery systems include transmucosal drug delivery (TMDD) systems for systemic drug administration, as well as systems which provide localized administration of the drug to the environment surrounding the mucous membrane. The systems are particularly advantageous for use in non-human animals having a condition ameliorated by the drug delivered. Generally, TMDD systems known in the art can be used according to the invention. However, the invention also provides preferred mucosal originated drug delivery compositions and some novel compositions which are particularly advantageous for use in certain animals for amelioration of certain conditions.

According to the invention, "mucous membrane" includes all mucous membranes in an animal's body including buccal, gingival, gastrointestinal, nasal, rectal, conjunctival, sublingual, urethral, ureteral, uterine, vaginal, cystic (bladder), etc. Body systems of an animal that can be treated according to the invention include cardiovascular, respiratory, gastrointestinal (GI), central nervous (CNS), immune, musculoskeletal, reproductive, urinary, integumentary, etc. As discussed below, conditions treated according to the invention include most diseases amenable to treatment with a pharmacological agent.

Administration across a mucous membrane (i.e. transmucosal) provides an alternative route for systemic absorption of many drugs and can be particularly advantageous for those that are only available in injectable form or have high first-pass hepatic metabolism. Drug release away from the mucosal surface provides for local administration of the drug to the environment and/or tissues surrounding the mucosal surface. Frequently the surrounding tissues also have a mucosal membrane surface.

In some embodiments, the drug delivery system, such as a TMDD system, can provide for bidirectional release of the drug. That is, the drug can pass out the TMDD towards the mucosal surface for systemic administration across the mucosal membrane and the drug can pass out the TMDD away from the mucosal surface for release into the environment surrounding the mucosal membrane, for example, into the oral cavity, vagina, surface of the eye, bladder, etc. Alternatively, the drug release system can provide for unidirectional delivery exclusively towards the mucosal membrane or exclusively away from the mucosal membrane. Some drug delivery systems can also provide a gradient to facilitate enhanced drug release towards the mucosal surface or away from the mucosal surface towards the surrounding environment.

The systems and methods disclosed are advantageous for all areas of animal care. However, it will be appreciated that often times the disposition, housing conditions, or restraint mechanisms unique to a particular specie will affect the choice of therapeutic regimen.

As used herein, the term "animal" encompasses all non-human animals including domestic and wild animals, such as non-human primates, farm animals, companion animals, marine animals, zoo animals, fur bearing animals, exotic animals, etc. Also the type of animal may be referred to by a group name such as "large," "small," "companion" or "exotic." The group name used is not intended to limit the described method of the invention solely for use in that group, but rather, is for purposes of explanation of a particular treatment regimen which may best be understood by reference to a characteristic exemplified by the named group.

Generally, the term "large animal" includes animals traditionally considered farm animals such as cattle, sheep, swine, poultry, horses, etc. These animals are often maintained as herds or flocks and may be subject to population health management programs. However, even within different large animal species or within the same species of large animal there are distinctions affecting choice of therapeutic regimen for a particular condition. For example, a condition in a free range beef cow who is infrequently handled may be treated significantly different than the same condition in a stanchioned dairy cow who is amenable to frequent handling for administration of a therapeutic agent. In addition, the intensive management programs of many swine and poultry operations are often not conducive to repeated handling which may be necessary for treatment or diagnosis of some conditions.

The term "small animal" generally refers to dogs, cats, ferrets and other animals kept as pets. The term "exotic animal" refers to animals including bears, tigers, lions, etc., which are typically not domesticated and may be kept in a zoo. "Marine animals" include whales, dolphins, manatee, sea lions, etc. As will be appreciated by one skilled in the art, some large animals, such as a horse, may be housed under herd conditions more typical of cattle while the housing of another horse may be more akin to a small animal pet. Thus, it is emphasized that the above groups should not be relied upon for phylogenetic accuracy but rather for convenience in discussing the various treatment methods disclosed herein.

I. Transmucosal Drug Delivery Systems

Transmucosal drug delivery systems suitable for the invention include known TMDD systems. Known TMDD systems are disclosed in, for example, U.S. Pat. Nos. 3,699,963; 3,972,995; 4,876,092; 4,900,552; 5,113,860; 5,578,315; 5,639,469; 5,688,520; and U.S. Pat. No. 5,780,045. A preferred group of TMDD's suitable for the invention are disclosed in U.S. Pat. Nos. 5,750,134 and 5,750,136. Generally, a TMDD as disclosed in these latter patents include a polymeric resin component dispersed in a hydrophobic elastomeric component.

Some preferred compositions for a TMDD according to the invention include a polyacrylic acid, a linear elastomer and a cross-linked elastomer. According to one such preferred embodiment, the polyacrylic acid can be Carbopol 971P or 974P, available from B.F. Goodrich. The linear elastomer can be polyisobutylene, VISTANEX® (LMMH), available from Exxon Chemical and the cross-linked elastomer can be Polysar Butyl XL 10,000 (80% cross-linked) available from Miles, Inc. Polyisoprene can also be added. Polyisoprene is available as NATSYN® 2210 from Goodyear Tire and Rubber Company.

The combination of Carbopol 971P or 974P with certain ratios of the cross-linked elastomer and polyisobutylene provides for an improvement in adhesive qualities of a mucosal drug delivery patch and drug release profiles that can be readily altered as needed for the particular drug to be delivered. Suitable ratios of LMMH: Polysar Butyl XL 10,000 are 1:2 to 5:1, preferably 3:1 to 5:1, more preferably 4:1. This embodiment is particularly advantageous for non-invasive drug delivery at a mucosal membrane in some animals, such as dogs, cats, horses, etc.

A pharmacological agent is preferably incorporated neat into a TMDD matrix composition of the invention. The pharmacological agent is preferably present in an effective amount, which will depend upon the particular agent used, the intended therapy, and the desired duration of use of a particular individual application of the composition containing the agent. Practical limitations on the amount of a pharmacological agent incorporated in a composition are that amount above which the composition begins to lose adhesion to a mucosal surface, and that amount below which a therapeutically effective blood level of drug cannot be achieved and/or maintained. Generally, the preferred range is from about 0.1% to about 25% by weight based on the total weight of the bioadhesive composition. Preferably, the drug will be capable of release from the composition in a sustained fashion over a prolonged period (i.e., at least about 6 hours and preferably at least about 12 hours).

In some embodiments, the composition of the TMDD can also include a penetration enhancer (PE). A PE preferably facilitates transfer of the drug from the TMDD through the mucous membrane into the systemic circulation. Facilitation of transfer can provide more rapid onset of action of the drug. However, in addition to facilitating drug transfer, the PE is preferably selected to avoid causing harm to the mucous membrane. Examples of penetration enhancers suitable for the invention include anionic surfactants (e.g., sodium lauryl sulfate); cationic surfactants (e.g., cetylpyridinium chloride); nonionic surfactants (e.g., polysorbate 80, polyoxeyethylene 9-lauryl ether, glycerol monolaurate); lipids (e.g., oleic acid); bile salts (e.g., sodium glycocholate, sodium taurocholate); and related compounds (e.g., sodium tauro-24,25-dihydrofusidate).

One preferred penetration enhancer for application to some mucous membranes is glycerol monolaurate, commercially available from Lauricidin, Inc., under the name Lauricidin®. Lauricidin® can be advantageously used in a TMDD system to (1) reduce the time necessary for on-set of drug action; (2) increase the amount of drug penetrating the mucous membrane: and (3) cause little or no deleterious effect on the mucous membrane. Further, Lauricidin® is compatible with many TMDD patch formulations and causes minimal milling problems in such applications.

As discussed above, a TMDD can provide for unidirectional transmucosal drug delivery. In one such embodiment, an inner core of a drug laden polymer can be contained within an outer region of an adhesive polymer containing no drug. The drug laden inner core and outer region are then covered with a thin layer of an impermeable adhesive film that effectively seals one surface of the inner core of drug containing polymer. The surface of the inner core which contacts the gingival mucosa lacks the impermeable layer of adhesive permitting drug release towards the mucous membrane.

The outer region of adhesive can be an adhesive polymer identical to the drug laden polymer, or formulated differently. One advantage of this two region system is that properties of the adhesive of the outer region of the patch can be changed without changing the drug releasing properties of the inner core polymer. Application of an impermeable film layer can also be used to control the swelling rate and dissolution of the patch thus increasing patch longevity under some circumstances.

As used herein, an "impermeable membrane" can be impermeable to the release of a drug incorporated in the TMDD. Thus, use of such an impermeable membrane can ensure that release of all drugs in the TMDD is towards the mucous membrane. Alternatively, an "impermeable membrane" can be impermeable to absorption into the TMDD of fluid in the environment surrounding the TMDD.

A TMDD can also include a "semipermeable membrane." If placed near the mucous membrane surface of the TMDD, the semipermeable membrane can be used to control the rate of drug release towards the mucous membrane and/or improve the local tolerance of the drug. If placed away from the mucosal surface of the TMDD, the semipermeable membrane can be used to control the absorption of fluids surrounding the TMDD.

A TMDD of the invention also includes a drug or "pharmacological agent." As used herein, the term "pharmacological agent" includes any agent or combination of agents which can be used to diagnose, cure, ameliorate or otherwise manage a condition in an animal or a human. Unless otherwise stated, the term "treat" or derivatives thereof including "treatment" or "treating" is used herein generically to indicate administration of a pharmacological agent to an animal for any reason. Use of the term "treat" is not intended to distinguish a therapeutic procedure from a diagnostic procedure from a palliative procedure, etc.

Examples of pharmacological agents according to the invention include, without limitation: anabolic agents (e.g., boldandiol, ethylestrenol, mibolerone, nandrolone, oxymetholone, stanozol, testosterone); antibacterial/antibiotics (e.g., aminoglycosides including: amikacin, apramycin, dihydrostreptomycin, gentamicin, kanamycin, neomycin, spectinomycin, vancomycin; cephalosporins including: cefaclor, ceftazidime, cephalexin, cephalothin; clindamycin; chlorhexidine, fatty acid monoesters, such as glycerol monolaurate; fluoroquinolones including enroflaxacin, ciprofloxacin; macrolides including erythromycin, lincomycin, tylosin; penicillins including amoxicillin with and without potentiators, ampicillin, hetacillin, ticarcillin; tetracycline and analogues; sulfanomides with or without potentiators including sulfachlorpyridazine, sulfadimethoxine, sulfamethazine, sulfaquinoxaline); antifungal (e.g., miconazle, itraconazle, griseofulvin, glycerol mono-laureate, metronidazole); anti-cancer (e.g., actinomycin-D, cisplatin, cytarabine, doxorubicin, 5-fluorouracil, methotrexate, pergolide, purine analogues, oncovin, vinblastine, vincristine); antidotes and reversing agents (e.g., atropine, 2-PAM, naloxone, nalorphineHCl, yohimbine, atipamazole); antihistamines (e.g., cromolyn sodium, diphenhydramine, pyrilamine, tripelennamine); antipyretics (e.g. acetaminophen); non-steroidal anti-inflammatory drugs (NSAID), (e.g., flunixin meglumine, acetylsalicylic acid, ibuprofen, ketoprophen, meclofenamic acid, naproxen, phenylbutazone, zileutin); steroidal anti-inflammatory drugs (e.g., beclomethasone, budesonide, dexamethasone, flumethasone, flunisolide, fluticasone, isoflupredone, prednisolone, triamcinolone); anti-thrombotics (e.g., acetylsalicylic acid); anti-tussives (e.g., narcotic analgesics, dextromethorphan, phlocodine); bronchodilators (e.g., atropine, albuterol, clenbuterol, pirbuterol, salmeterol, fenoterol, aminophylline, glycopyrrolate, terbutaline, theophylline); parasympathomimetics (e.g., bethanechol); anticholinergics (e.g., atropine, ipratropium, tiotropium); anti-virals (e.g. pyrimidine nucleosides including idoxyuridine, trifluridine; purine nucleosides including: vidarabine, acyclovir; ribaviran, amantadine, interferon and its inducers, and other miscellaneous anti-virals, for example, thiosemicarbazones, zidovine, benzimidazoles); sympathomimetics (e.g., epinephrine); cardiovascular agents (e.g., calcium channel blockers: diltiazem, nifedipine, verapamil); anti-arrhythmics (e.g., alprenolol, amiodarone, bretylium, diltiazem, flecainide, isoproteronol, lidocaine, metoprolol, nadolol, procainamide, propranolol, quinidine, timolol, verapamil); vasoactive drugs (e.g., caprotil, epinephrine, hydralazine, isoxsuprine, nitroglycerin, pentoxyfylline, phentolamine, prazosin); cardiotonics (e.g., dobutamine; dopamine; digitoxin; digoxin); central nervous agents: e.g., anesthetics including barbiturates; anticonvulsants e.g., clonazepam, diphenylhydantoin, primidone; antidepressants: e.g., SSRI (selective serotonin re-uptake inhibitor); anti-emetics: e.g., domperidone, metoclopramide; emetics: apomorphine; narcotic analgesics: codeine, demerol, fentanyl, hydrocodone, meperidine, morphine, oxymorphone, butorphanol, buprenorphin pentazocine; non-narcotic analgesics including acetominophen, aspirin, dipyrone; respiratory stimulants: e.g., caffeine, doxapram, zolazepam; sedatives/tranquilizers including: barbiturates; alpha 2 antagonists (e.g., detomidine, medetomidine, dexmedetomidine, carfentanyl, diazepam, droperidol, ketamine, midazolam, phenothiazine tranquilizers (including acepromazine, chlorpromazine, ethylisobutrazine, promazine, trifluromazine), romifidine, xylazine; diuretics (e.g., chlorthiazide, furosemide); dental hygiene (e.g., glycerol monolaurate materials and orally active antibiotics); gastrointestinal (e.g., cimetidine (H2 agonist), famotidine, ranitidine, omeprazole); hypotensives (e.g., acepromazine, phenoxybenzamine); hormones (e.g., ACTH, altrenogest, estradiol 17β, estrogens GNRH, FSH, LH, insulin, LHRH, megestrol, melatonin, misoprostol, norgestomet, progesterone, testosterone, thyroxine, trenobolone); immunomodulators (stimulants including: levamisole, imiquimod and analogues, biological derivative products; and suppressants including: azathioprine); internal parasiticides (e.g., ivermectin, mebendazole, monensin, morantel, moxidectin, oxfendazole, piperazine, praziquantel, thiabendazole); miotics (e.g. acetylcholine, carbachol, pilocarpine, physotigmine, isoflurophate, echothiophate, prolidoxime); mydriatics (e.g., epinephrine, phenylephrine); mydriatics/cycloplegics (e.g. atropine, scopalamine, cyclopentolate, tropicamide, oxyphenonium); prostaglandins (e.g., cloprostenol, dinoprost tromethamine, fenprostalene, fluprostenol); muscle relaxants (e.g., aminopentamide, chlorphenesin carbamate, methocarbamol, phenazopyridine, tiletamine); smooth muscle stimulants (e.g., neostigmine, oxytocin, propantheline); serotonin; urinary acidifiers (e.g., ammonium chloride, ascorbic acid, methionine); vitamins/minerals (e.g., Vitamins A, B, C, D, K, E); etc.

A TMDD can include one or more drugs. In addition, the surface area, shape, and thickness of a drug delivery device can vary based on: the size and/or shape of the mucous membrane, the design of the device (e.g., matrix or reservoir), desired drug delivery rate, site of drug action (e.g., local or systemic), duration of adhesion, desired drug delivery concentration, desired duration of drug release, amount of drug, etc. Examples of suitable shapes include parallelograms (e.g., squares, rectangles), trapazoids, triangles, circles, ovals, etc.

II. Mucosal Membranes

Mucosal membranes are located throughout animal and human bodies and generally line the surfaces of body cavities. The mucosal membranes function, in part, to control the entry and exit of substances along the surface area of the body cavity. Thus, mucous membranes can act as a barrier to control water loss from body cavity surfaces as well as prevent entrance into the body of foreign substances including infectious agents, toxins, allergens, etc. Examples of mucosal membranes suitable for the method of the invention include, without limitation, buccal, gingival, gastrointestinal, nasal, rectal, conjunctival, sublingual, urethral, ureteral, uterine, vaginal, bladder, etc.

While mucosal membranes share many common functions, some differences exist between mucosal membranes at different locations in the body. These differences may provide unique characteristics to the body system with which the mucous membrane is associated. For example, in addition to functioning as a barrier, mucous membranes lining the small intestine also include cellular mechanisms for breakdown of carbohydrates, proteins and other polymeric nutritional substances which are absorbed by the gut. The differences between mucosal membranes at different locations may require modification of the TMDD to address the nuances of the particular membrane. In addition, even in a particular location, cells comprising the mucous membranes have characteristics that are unique to the particular membrane. For example, in the oral cavity, the gingival membrane is a thin keratinized epithelium whereas the buccal membrane is a thick non-keratinized epithelium. Consequently, all mucous membranes in the oral cavity do not have a uniform permeability due to differences in epithelial morphology.

However, the overall increased permeability of mucous membranes relative to the skin as well as the lack of hair or other diffusion inhibiting structures makes the mucous membranes an advantageous portal of entry for drug delivery in animals since it by-passes presystemic metabolism by the gastrointestinal tract and hepatic first-pass elimination. Moreover, the accessibility of certain mucous membranes for certain treatment applications advantageously provides increased therapeutic and diagnostic options due to increased convenience, safety or accessibility to a systemic drug administration route.

III. Conditions Treated

The device and methods disclosed herein can be used to treat many systemic or localized conditions of an animal's body through local or systemic administration of a pharmacological agent. As used herein, the term "condition" generically refers to any infectious, non-infectious, pathological, physiological, psychological, biochemical or other state of any part of an animal's body that can be diagnosed, cured, prevented, exacerbated or otherwise modified by a pharmacological agent incorporated into a drug delivery device according to the invention. Typically, the methods disclosed herein will be particularly advantageous for administering a therapeutic agent to an animal to remedy or otherwise ameliorate a condition in the animal.

The invention is particularly advantageous for conditions requiring sustained drug release over a period of time commensurate with the duration of drug release of a particular device. For any particular condition to be treated, the mucosal membrane selected for application of a drug delivery device may vary based on factors including: the treatment result desired, accessibility of the membrane, facilities available for handling or restraining the animal during application or removal of the device, as well as convenience, safety and skill level of the treatment administrator.

In addition, a drug delivery device can be optimized for a particular use. In addition to the condition in need of treatment, factors which may be considered in optimizing the device for a particular use include age, breed, body weight, sex or temperament. Characteristics of the device which may be manipulated for a particular use include thickness, surface area, duration of adhesion, duration of release, drug composition, release rate, release direction, release gradient, swelling, etc.

The following description of conditions which can be treated according to the invention is not intended to be exhaustive. Rather, the description provided is intended to provide examples of advantageous methods according to the invention.

A. Central Nervous System Conditions

The invention can be used to directly treat a condition of the central nervous system (CNS) including, for example, seizures, depression, ataxia, undesirable behavior (e.g., excitement, fear, aggression), nausea, emesis, etc. The invention can also be used to treat other conditions of the body through the CNS, by providing for example, analgesia of peripheral pain, emesis inducement, muscle relaxation, sedation, chemical restraint, etc.

1. Sedation

Animals are frequently sedated during performance of some veterinary diagnostic or therapeutic procedures including minor surgical and dental procedures. In addition, sedation can be advantageously used to reduce anxiety during transportation, grooming, or housing. Frequently, these latter procedures are performed by an animal owner, trainer, or handler who may not be skilled in parenteral drug administration by, for example, the subcutaneous (SC), intravenous (IV) or intramuscular (IM) route. And, while many sedative agents are available in an oral form, often times it is difficult to control the onset of effect as well as the level of sedation provided through an orally administered drug.

However, applying a TMDD containing a sedative to a mucous membrane provides for easy administration of the drug with only minimal skill necessary for application. As described herein, onset and level of sedation can be controlled by the drug selected, quantity of drug in the device, presence of penetration enhancers, design of the device, size or thickness of the device, etc. Duration of drug effect can be controlled by the quantity of drug in the device or duration of application of the device. Thus, the effect of the drug can be terminated by simply removing the TMDD from the mucous membrane.

In a typical application for a companion animal, a sedative containing device can be applied to an oral mucous membrane such as the buccal or gingival membrane. However, in some large animals, such as horses and cattle, the nasal mucosa can also be used. In addition, the vaginal or rectal mucosa may provide a suitable application site in large animals (e.g., horses, cattle or pigs), wild animals, zoo animals, etc.

In one embodiment, a method of the invention provides a TMDD application for ameliorating transportation anxiety. Such an application may be beneficial for long term transport by sea, air or land, as well as for a short car ride that may be loathed by cats, dogs or other animals not accustomed to this activity. Depending on the relevant laws and regulations, a sedative containing TMDD may be made available to the animal owner or handler from a veterinarian for use as necessary.

Often times, transporting a large animal, such as a horse, causes excitement and stress which can be hazardous to both the horse and the horse handler. By application of a sedative containing TMDD, the horse can be lightly sedated to relieve the animal's stress or anxiety as well as relieving the stress and potential hazard to the handler.

Other sedative uses for TMDDs according to the invention include, for example, post-parturient aggressiveness or anxiety in small or large animals, post surgical anxiety amelioration, post surgical mobility, stress related agitation or aggression, etc.

Suitable sedatives for use with a TMDD include, for example, diazepam, promazines, xylazine, barbiturates, etc. One particularly advantageous sedative for use in animals is medetomidine. Medetomidine and related compounds detomidine, and dexmedetomidine are known $\alpha_2$ agonists used as a sedative and/or analgesic in animals. For further discussion of these compounds reference is made to Stenberg D., "Physiological Role of $\alpha_2$-adrenoceptors in the Regulation of Vigilance and Pain: Effect of Medetomidine," *Acta Vet. Scand.*, 85 (1989); Hamline Robert L. et al., "Studies to Determine the Optimal Dose of Medetomidine," *Acta Vet. Scand.*, 85:89–95 (1989); and Söbchel, W. et al., "Sedation and Analgesic with DOMOSEDAN® (Detomidine HCl) in Horses: Dose Response Studies on Efficacy and its Duration," *Acta Vet. Scand.*, 82:69–84 (1986).

The appropriate concentration of medetomidine and other sedatives for use in a TMDD can be based on available known therapeutic dosage data. In addition, the Examples of the invention provide several TMDD compositions containing varied concentrations of medetomidine, providing varied release rates for different pharmacological affects.

2. Analgesia

Known centrally and peripherally acting analgesics can also be transmucosally administered according to the invention. In addition to medetomidine and related $\alpha_2$ adrenergics, other centrally acting analgesics suitable for the invention include, for example, butorphanol, buprenorphin, morphine, etc. Peripherally acting analgesics include, for example, NSAID, corticosteroids, etc.

Conditions amenable to analgesic administration via a TMDD of the invention include post-surgical pain. For example, orthopedic surgery is typically associated with extreme post-surgical pain that can require repeated injection of analgesic drugs. By applying TMDD containing an analgesic to a mucosal membrane, such as a gingival membrane, sustained drug delivery may be provided for up to 24 hours or more. Use of this method can significantly reduce the around the clock nursing associated with many medical or surgical conditions of animals.

Other conditions where TMDD delivery of an analgesic agent can be advantageously used in animals includes, for example, gastrointestinal pain such as colic in horses (discussed below), musculoskeletal pain, thoracic pain, pain associated with generalized trauma, any type of pain associated with surgery, etc.

3. Other

TMDDs can also be used for treatment of other conditions which originate from or can be ameliorated via a CNS mediated mechanism. One such condition is seizuring. In the case of a small animal, such as a dog affected with epilepsy or other condition causing recurrent seizures, a seizure can occur at home. Generally, the fastest route for administration route providing the quickest effect of an antiseizure medication is intravenously. Unfortunately, in a majority of cases, the pet owner who may be present during such a seizure is unlikely to be skilled at administering an IV injection. Oral administration is unlikely to be feasible because of the slow onset of action and the potential danger in view of the muscle contractions occurring during the seizure, particularly the muscles of mastication. However, by having a TMDD available that contains an antiseizure medication, an accessible mucosal membrane such as the gingival, buccal, vaginal or rectal membrane can permit safe and effective administration of the drug. It will be appreciated that such an application for a TMDD could also be useful in a human patient. Suitable antiseizure drugs are recited above and include, for example, phenobarbital, diphenylhydantoin, primidone, clonazepam, etc.

Centrally acting emetic and anti-emetic drugs can also be administered according to the method of the invention. For example, in one embodiment, a TMDD can be provided with an emetic drug. The TMDD could be available separately or as part of an emergency kit for use in the event of ingestion of a toxic substance by an animal or human.

A TMDD can also be provided with a centrally acting respiratory stimulant such as doxapram.

Other conditions which can be treated via a CNS mechanism and which may not have been specifically mentioned herein will be appreciated by one skilled in the art and are included within the scope of invention.

C. Ophthalmic Conditions

One advantageous use of the present invention is for treatment of certain ophthalmic conditions amenable to treatment with a TMDD. In many instances, the disclosed ophthalmic conditions amenable to treatment with a TMDD in an animal will be equally beneficial for humans.

Ophthalmic conditions amenable to treatment according to the invention include keratitis, conjunctivitis, uveitis, iridititis, scieritis, etc. The conditions can be infectious, traumatic, congenital, surgical or immune mediated in origin. Some well known examples of conditions which can be treated according to the invention include corneal ulcers, pink-eye, particularly in cattle, recurrent uveitis (moon-blindness) in horses, iridocyclitis, glaucoma, orbital cellulitis, chronic superficial keratitis, etc.

One common element of many ophthalmic conditions is the need for frequent treatment readministration. Often times in acute inflammatory or infectious ophthalmic conditions, treating 6 to 8 or more times a day is not uncommon. In adult humans the need for frequent readministration of drops, ointments or other form of ophthalmic medicament is inconvenient. In a child repeat administrations can be trying at best. In some animals, it can be dangerous. In addition, many times, particularly in zoo animals, wild animals, horses or other large animals, treatment administration can require at least two people for each administration. The ability to stay with the animal for repeat treatments throughout the day may not be feasible for the animal owner. Moreover, retaining one or more people to treat the animal or hospitalizing the animal for eye drop administration can be expensive.

In some cases, reducing the frequency of treatment administration in humans or animals due to difficulty, inconvenience, or other reason, will prolong the healing process. Moreover, if sedation is necessary for treatment of a fractious horse, scared dog or a dangerous exotic animal, treatment of the eye brings with it the repeated need for sedation.

In one embodiment, the present invention can facilitate healing of an ophthalmic condition by providing sustained release of the necessary ophthalmic medicament through a drug delivery device of the invention. According to this embodiment, the drug delivery device is typically applied to the conjunctival mucosal tissue. For some conditions where topical application of the pharmacological agent is desired, the delivery device can provide for unidirectional release toward the surface of the eye and away from the mucosal membrane. In some conditions, bidirectional release may be desired.

Generally, the device can be applied to the conjunctival mucosa anywhere between the edge of the eyelid and the conjunctival cul de sac. Obviously, in the case of a corneal lesion, such as an ulcer, the device should be placed on the conjunctival membrane in a location which will avoid further irritation of the lesion when the lids open and close. Foreseeably, there may be occasion to apply the delivery device to the corneal or scleral surface of the eye.

While conjunctival application of a device may be a preferred membrane sight for treatment of ophthalmic conditions, it can also be advantageous for some non-ophthalmic conditions requiring systemic treatment. According to this embodiment, a TMDD can provide drug release through a bidirectional device or a unidirectional device providing release towards the mucosal membrane. Examples of conjunctively applied TMDDs for systemic effects include sedation, analgesics, etc.

Any drug typically used for treatment of an ophthalmic condition can be incorporated into a conjunctival patch including antibiotics, steroids, mydriatics, cycloplegics, etc.

D. Respiratory Conditions

The present invention also provides for treatment of a respiratory condition in an animal. Such conditions include infectious conditions, immune mediated, mechanical causes, etc. According to this embodiment antibacterial, antiviral, antiprotozoal or other pharmacological agent effective in eliminating an infectious agent can be included in a TMDD of the invention. In addition, corticosteroids, beta blockers, α or β adrenergics, antihistamines, anticholinergics, leukotriene antagonists, lipoxygenase inhibitors or other drugs that are effective in the treatment of inflammatory or immune mediated respiratory conditions, such as allergies, small airway disease, chronic obstructive pulmonary disease, asthma, bronchitis, influenza, etc., can be included in a TMDD of the invention. The TMDD may be optimized for application and drug delivery to any suitably accessible mucous membrane.

According to this embodiment, stress to the animal or animal care provider as well as the inconvenience associated with frequent readministration of many effective therapeutic agents for respiratory conditions can be avoided. In addition, often times the barns which house cattle or horses are poorly ventilated, contain high levels of ammonia or high levels of mold spores, or hay or grain dust that can exacerbate a respiratory condition. Under these and other circumstances, the healthiest environment for recuperation of the condition is outdoors. However, the need for frequent drug readministration, convenience, cost or lack of personnel may dictate maintaining the animal indoors. Not only can this reduce therapeutic efficacy, it can also prolong the duration of therapeutic intervention.

Thus, by providing a selected therapeutic agent in a TMDD according to the invention, the need for frequent handling for repeat treatment can be reduced and the consistency of overall blood levels of the therapeutic agent maintained. Moreover, in some circumstances, by allowing the animal to be in a well ventilated environment during treatment, overall convalescence time for the respiratory condition can be reduced.

E. Cardiovascular Conditions

The present invention also provides for treatment of a cardiovascular condition in an animal. Such conditions include, for example, cardiomyopathies, dysrhythmias, hypertension, hypotension, congestive heart failure, etc. The TMDD may be optimized for application and drug delivery to any suitably accessible mucous membrane and include an cardiovascular agent such as propanolol verapamil, nitroglycerin or other drug as listed above.

F. Gastrointestinal Conditions

The present invention further provides for treatment of a gastrointestinal (GI) condition in an animal. Such conditions include, for example, GI hypermotility, GI hypomotility, GI spasm, GI ulcers, parasitism, etc. The TMDD may be optimized for application and drug delivery to any suitably accessible mucous membrane and include drugs such as neostigmine, metaclopramide, cimetidine, or others listed above.

In some embodiments, the invention is particularly suited for treatment of gastrointestinal diseases in horses. In horses, gastrointestinal conditions associated with pain are generally referred to as colic. Often times the presenting signs of an afflicted animal are similar even though the origin can be the stomach, small intestine or large intestine. Classic signs include increased heart rate, increased respiratory rate, pawing, rolling and kicking at the abdomen. The duration and persistence of the clinical signs can provide the veterinarian with significant information for determining a cause, implementing a therapeutic plan and making an accurate prognosis.

Some causes of colic, such as an impaction (fecal, sand, etc.), GI hypermotility, GI spasm, gastric dilation, gastric ulcers, parasitism, etc. can be managed medically. Others, such as intussuseptions, torsions, volvuli or other GI displacement conditions typically require surgical intervention. However, early in the course of the disease it may be difficult to determine whether the animal will be best managed medically or surgically. Thus, when the animal first begins to show clinical signs of colic, it is important that proper therapy be implemented to alleviate the pain and reduce the chance of injury to the horse or attending personnel. In some instances, therapy may be administered by the owner or other farm personnel while waiting for the veterinarian to arrive. In these situations, it is also important that the therapy administered does not excessively mask signs which will assist the veterinarian in making a diagnosis.

Analgesic therapy for equine colic are typically administered IV, IM or orally. When given orally, onset of therapeutic effect may be slow. If skilled personnel are available, IV administration provides a more rapid onset. However, in a case where repeated treatment is necessary repeated injections are undesirable. In foals, repeated injections can be particularly stressful for all involved.

Advantageously, the method of the invention provides for relatively rapid onset of therapeutically effective dosages of an analgesia without the need for injection. Thus, the skill level necessary for the care giver is reduced. In addition, the sustained drug release provided by a TMDD reduces the need for repeat treatment. If the colic persists and additional treatment is needed, application of one or more subsequent TMDDs can be done with less stress for all involved. If termination of analgesic therapy is desired, the TMDD can be removed.

It is foreseen that the use of a TMDD containing an analgesic will be useful in treatment of all types of colic including impaction colics in adult horses. The method will also be particularly advantageous for use in neonatal foals with colic due to retension of meconium or other impaction condition. In addition, once the analgesic has provided an adequate therapeutic effect, the foal can be turned out into a paddock with the mare with reduced risk of injury from rolling, kicking or pawing near a fence, tree or other object that could harm the foal. Reevaluation of the clinical signs, without masking interference of the analgesic agent, can be provided by simply removing the TMDD.

Many times a horse effected with a surgical colic condition will need to be transported to a surgery facility. During transport, it is often necessary to provide continuous pain relief to prevent the animal from injuring itself in the transport vehicle. Application of a TMDD containing an analgesic or an analgesic/sedative combination as a single or multiple drugs can provide sustained drug release to alleviate the pain or anxiety during transportation.

A TMDD for gastrointestinal conditions can be applied to any suitable mucous membrane including the oral, nasal, gastric, intestinal, colonic, vaginal, rectal, etc. Any known analgesic can be included in a TMDD for treatment of colic including non-steroidal anti-inflammatory agents such as phenylbutazone, flunixin meglumine or xylazine, demetomidine, butorphanol, ketoprofen, pentazocine, meperidine, etc. A selection of TMDDs will be available providing different concentrations and release rates of the agent depending on the size of the animal, severity of the pain and desired duration of effect.

G. Musculoskeletal Conditions

The present invention also provides for treatment of a musculoskeletal condition in an animal. Such conditions include, for example, myositis, arthritis, tendinitis, bursitis, laminitis, trauma, etc. The TMDD may be optimized for application and drug delivery to any suitably accessible mucous membrane and include drugs such as corticosteroids, NSAIDs, muscle relaxants, etc. as listed above.

H. Reproduction

The present invention can also be used for treating, modifying or otherwise altering conditions of the reproductive system of animals. According to this embodiment, the drug delivery device can provide for bidirectional release of a pharmacological agent or unidirectional release across a mucous membrane for transmucosal administration from an oral, vaginal, rectal, etc., location. Alternatively, the agent can be unidirectionally released away from the mucosal surface into the environment surrounding a mucosal surface such as the vagina, uterus, etc.

According to this embodiment, a TMDD can include any drug suitable for treatment of a particular reproduction condition. In some embodiments, the TMDD can include an antibacterial, antifungal, antiviral or other agent for treatment of infectious conditions. In other embodiments, the device can include hormones or other agents for inducing estrus such a prostaglandin $F2_\alpha$, melatonin, etc. In another embodiment the TMDD can provide for administration of abortificacients such as prostaglandin $PGF2_\alpha$, diethylstilbesterol, oxytocin, etc., to eliminate unwanted pregnancies.

In one embodiment, it is foreseen that a TMDD can include a hormone such as estrogen, progesterone, lutenizing hormone, follicle stimulating hormone, altrenogest, etc. for synchronization of estrous among a group of animals.

A TMDD can also be advantageously used for periparturient conditions. TMDDs useful in the periparturient period can include hormones or other agents which can assist in inducing parturition increasing uterine contractions for expelling a retained placenta, etc. (e.g., oxytocin), decreasing uterine motility when there is a potential for post-partum uterine prolapse etc. A TMDD can also include oxytocin, domperidone, etc. for post-partum agalactia or other failure of milk let down.

I. Immune Conditions

The invention also provides for treatment of an immune system condition. In one such embodiment, the TMDD can include an agent which provides for suppression of a hyperactive immune response, allergies etc. Suitable agents include, for example, steroids, anithistamines, leukotriene antagonists, lipoxygenase inhibitors, interferon, epinephrine or other drug listed above.

A TMDD can alternatively include immune system stimulants or facilitators for enhancing the immune response. Suitable compounds for this embodiment include, for example, levamisole, imiquimod, etc.

In another embodiment, the TMDD can include an antigen (immunogen) for immunizing an animal against the antigen. As with other embodiments disclosed herein, the TMDD can be constructed for release of the antigen across the mucosal membrane for systemic immunization, or away from the mucosal membrane for stimulation of mucosal surface immunity.

As used herein, the term "antigen" means a substance or entity that is structurally or functionally capable of inducing an immune response in an animal. Hence, an antigen includes, but is not limited to, inactivated whole microorganisms, attenuated whole microorganisms, whole viral particles, antigenic microorganism/viral components or fragments, chemically or physically modified antigens, recombinant antigens, and other antigens or combinations thereof.

J. Other

Some additional uses for a TMDD in animals include, for example, agents to treat metabolic conditions such as diabetes mellitus, vitamin deficiencies, etc. A device of the invention can also provide for release of anthelmentics, diuretics, vitamins or other nutrients, etc. It is also foreseen that the devices and methods disclosed herein could be advantageously used when a patient must be weaned from a drug gradually. For example, after cessation of corticosteroid therapy, a series of TMDDs can be used that provide incrementally reduced release of corticosteroids to wean the patient without severe generalized metabolic conditions associated with abrupt corticosteroid withdrawal.

EXAMPLES

Example 1

Preparation of a TMDD Matrix

Table 1 and 2 list TMDD formulations made with differing ratios of polyacrylic acid, polyisobutylene (PIB), polyisoprene (PIP) and XL-10,000. Polyisobutylene is available as VISTANEX® LMMH from Exxon Chemical. A preferred polyacrylic acid is Carbopol 971P NF available from B.F. Goodrich. Carbopol 971P is lightly cross-linked to provide a "fishnet" hydrated gel structure. In contrast, Carbopol 934P contains benzene and is more highly cross-linked resulting in a "fuzzball" gel structure. Polyisoprene (PIP) is available as NATSYN® 2210 from Goodyear Tire & Rubber Company. XL-10,000 is a pre-cross-linked butyl terpolymer rubber available from Miles, Polysar Rubber Division of Miles, Akron, Ohio.

Using a conventional two roller mill, PIB was pressed until a thin coating was maintained on the roller. PIP or XL-10,000 was then milled into the PIB until evenly distributed. Carbopol was added in small increments as the milling process continued. The developing sheet of polymer was removed by knife and formed into a ball. The ball was placed back onto the rollers which again mixed and pressed the polymer into a thin sheet. This process was repeated until all Carbopol has been thoroughly mixed into the matrix.

If incorporated, a pharmacologic agent can first be ground to reduce its particle size to about 2–100 μm. It can then mixed with the Carbopol for five minutes to create an even dispersion of drug with the Carbopol powder. Carbopol is dehydrated at 80° C. for one hour under vacuum prior to the addition of drug. Generally, if the moisture content of Carbopol is less than about 2%, dehydration is not needed.

Upon completion of milling, the polymer matrix was pressed into 20 mil (508 μm) sheets. After allowing for relaxation of the polymer, an acrylate pressure sensitive adhesive coated polyurethane film (e.g., TEGADERM® surgical dressing available from 3M Co.) was applied to one side. Discs of 12 mm diameter were punched out. These discs were then tested for swelling, adhesive qualities, drug release profile and efficacy.

Figure 2:
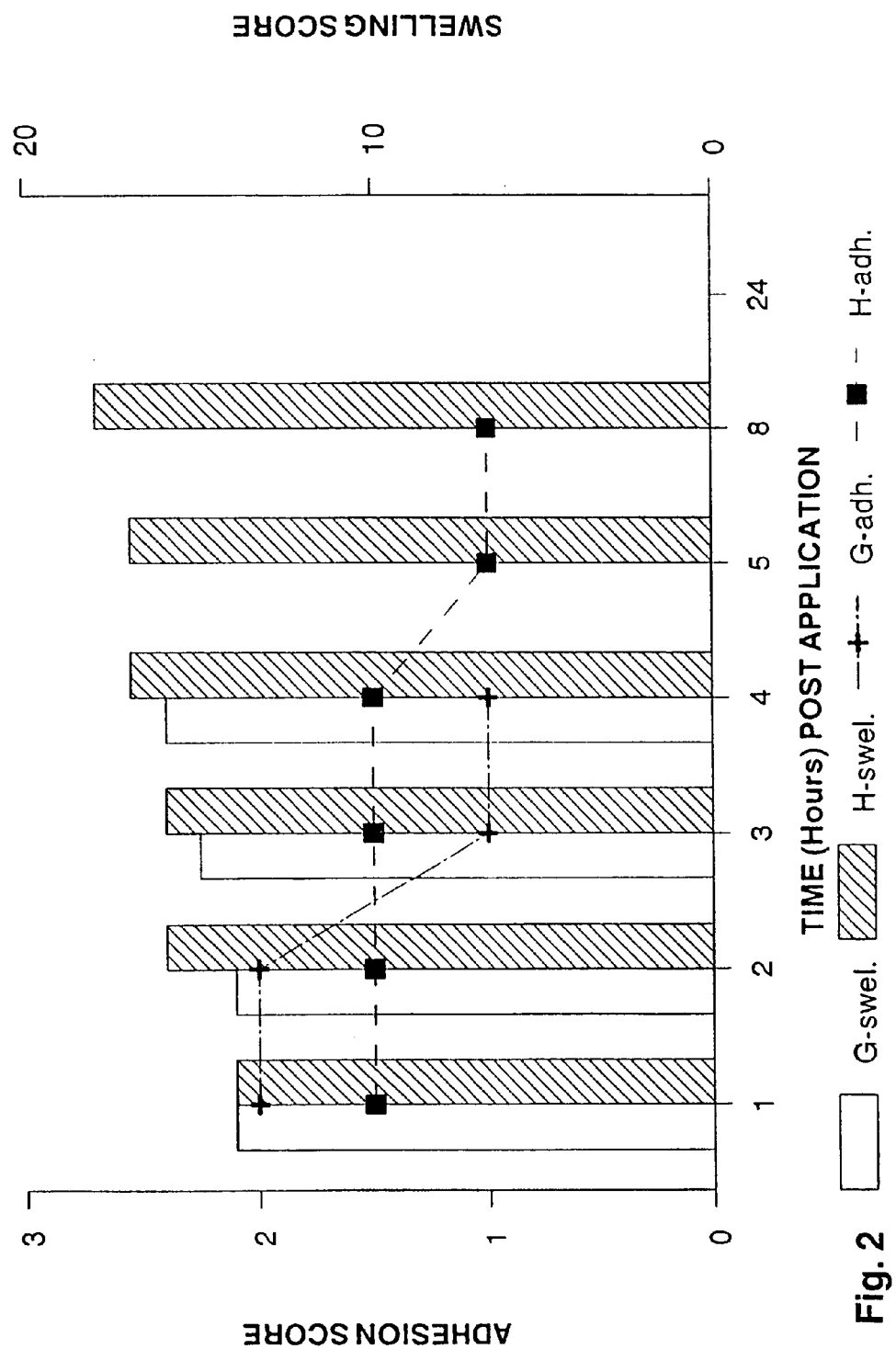
FIG. 2 is a graph illustrating adhesion and swelling scores of one embodiment of a transmucosal drug delivery system adhered to the buccal mucosa in canines.
Figure 3:
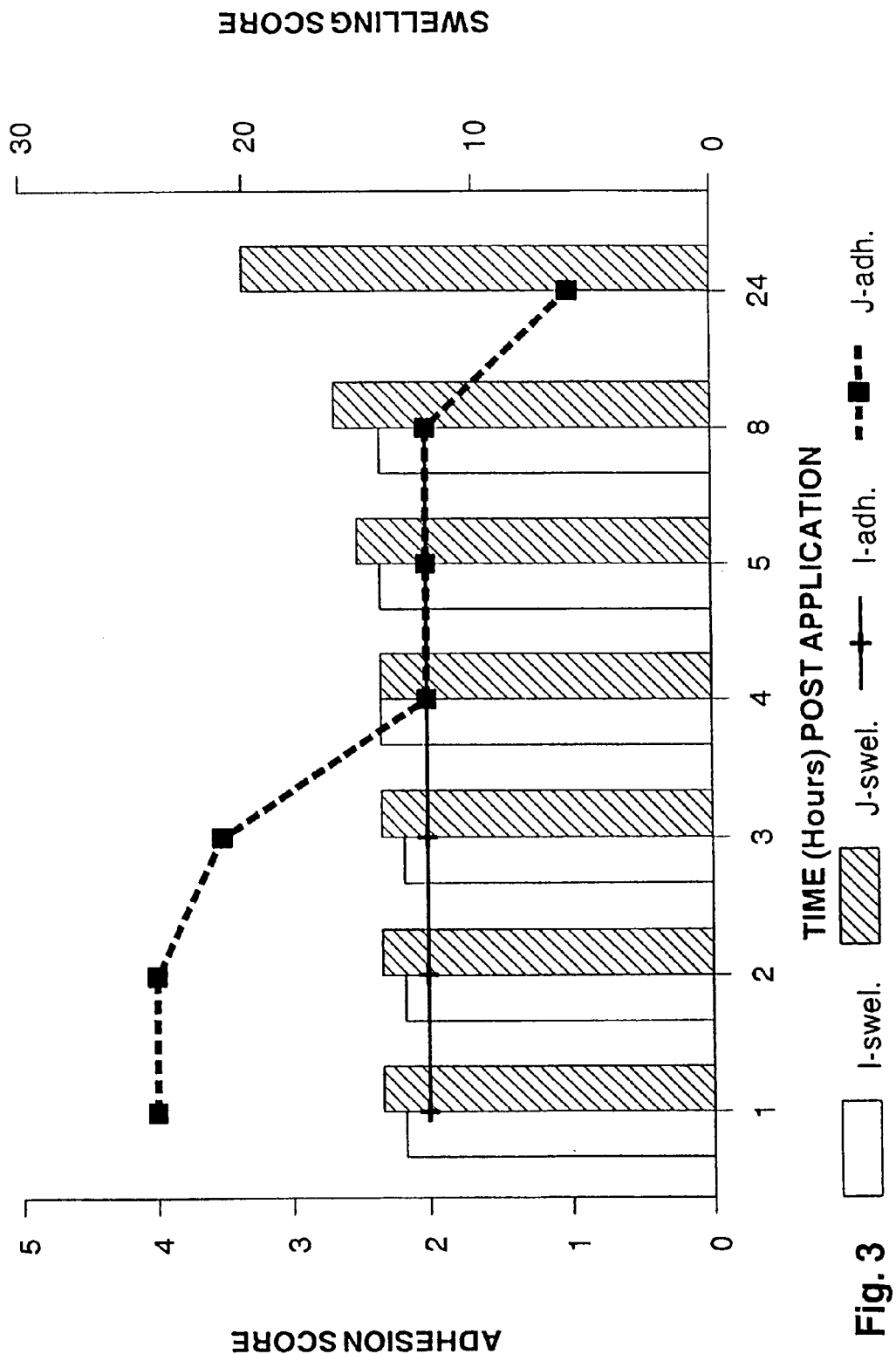
FIG. 3 is a graph illustrating adhesion and swelling scores of one embodiment of a transmucosal drug delivery system adhered to the buccal mucosa in canines.

Table 1 and FIGS. 1–3 illustrate the difference in adhesive qualities (in-vivo: see below for how scored) between Carbopol 934P and 971P in identical formulations.

TABLE 1

PATCH FORMULATION - C971P VS. C934P

| FORMULATION ID | COMPONENTS | PERCENTAGES/50 g lot |
|---|---|---|
| A | PIB | 20 |
|   | XL 10,000 | 15 |
|   | C934P | 65 |
| E | PIB | 20 |
|   | XL 10,000 | 15 |
|   | C971P | 65 |
| G | PIB | 43 |
|   | PIP | 7 |
|   | C934P | 50 |
| H | PIB | 43 |
|   | PIP | 7 |
|   | C971P | 50 |
| I | PIB | 43 |
|   | PIP | 7 |
|   | XL 10,000 | 10 |
|   | C934P | 40 |
| J | PIB | 43 |
|   | PIP | 7 |
|   | XL 10,000 | 10 |
|   | C971P | 40 |

TABLE 2

IN VITRO DRUG RELEASE STUDY: POLYMER RATIO EFFECTS

Weight %

| FORM ID | PIB:XL RATIO | PIB | XL 10,000 | 971P | PIP | ANTIPY. (%) |
|---|---|---|---|---|---|---|
| R | 4:1 | 40 | 10 | 48 | 0 | 2 |
| S | 1:1 | 25 | 25 | 48 | 0 | 2 |
| T | 4:1 | 40 | 10 | 40 | 8 | 2 |
| U | 1:1 | 25 | 25 | 40 | 8 | 2 |
| V | 2:1 | 30 | 15 | 53 | 0 | 2 |
| W | 0.5:1 | 15 | 30 | 53 | 0 | 2 |

FIGS. 1–3 illustrate the difference in in-vivo adhesive and patch swelling scores for the six formulations listed in Table 1. The values represent the average score for three patches for each formulation lot. These patches were applied to the gingival tissue in a dog and scored at each time interval for increased diameter and degree of adhesion to the gingival tissue. The adhesion score is derived by determining how many "sides" of the patch were still attached to the gingival tissue. A "side" is one-fourth of the circumference. The swelling score is the diameter of the patch (baseline diameter=12 mm).

Figure 4:
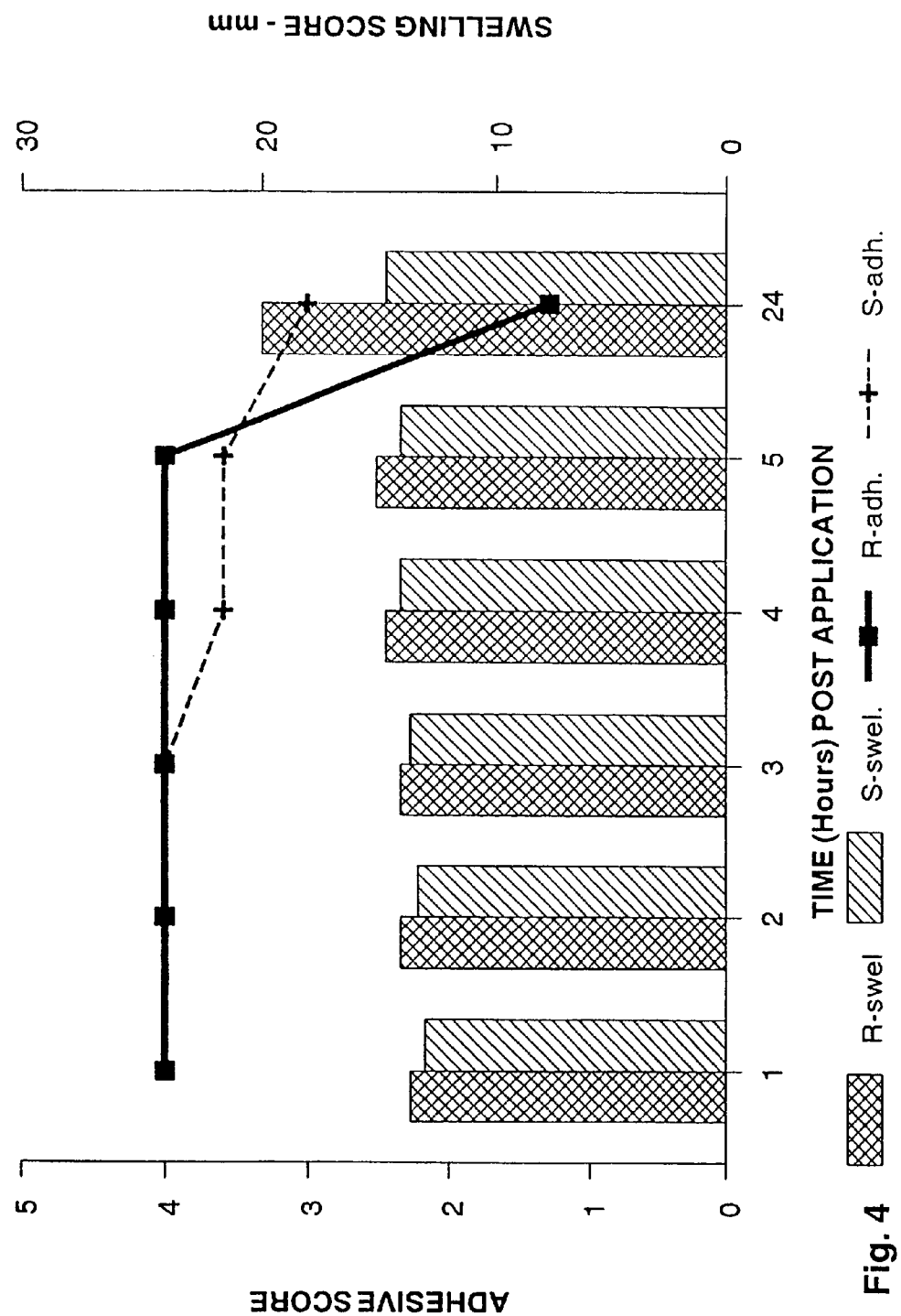
FIG. 4 is an in vivo comparison of transmucosal drug delivery formulations.
Figure 5:
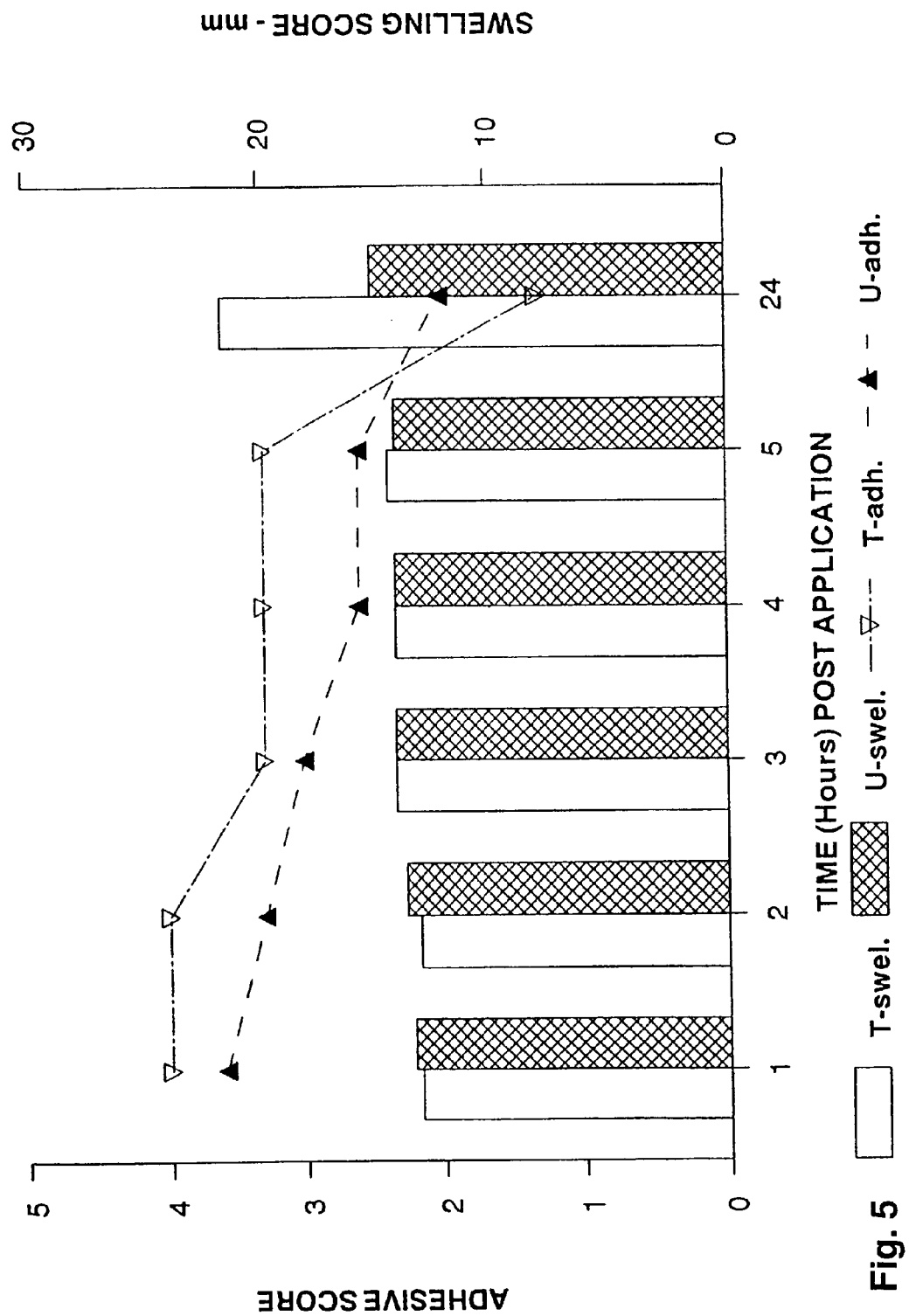
FIG. 5 is an in vivo comparison of transmucosal drug delivery formulations.
Figure 6:
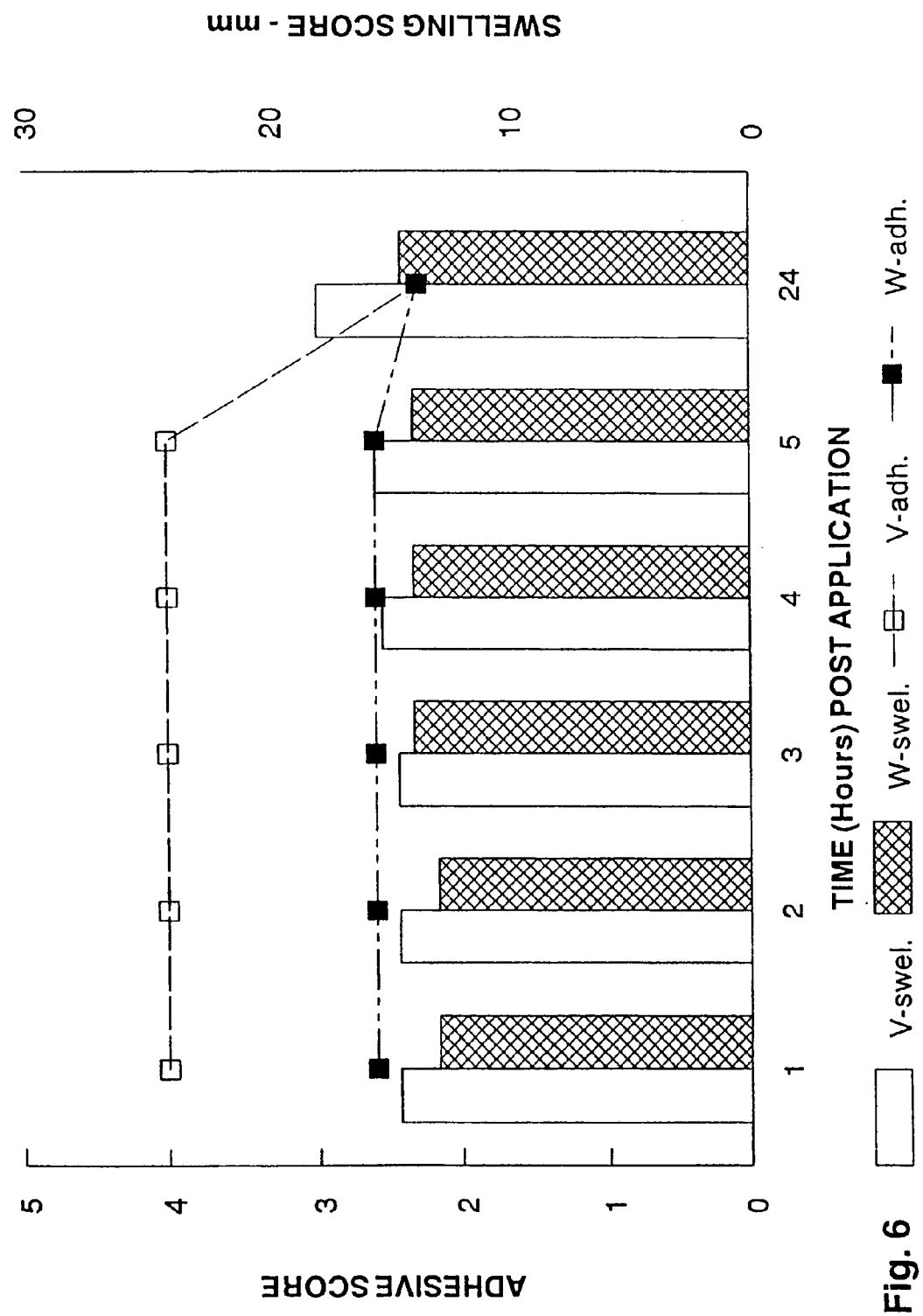
FIG. 6 is an in vivo comparison of transmucosal drug delivery formulations.

FIGS. 4–6 illustrate the in-vivo adhesive and patch swelling scores for the six formulations listed in Table 2. The values represent the average score for three patches from each formulation lot. Application of the patches and method of scoring are as described above for FIGS. 1–3. Formulations R, S, and V demonstrated excellent adhesive qualities for the duration of the study. Formulation W was inferior to all other formulations with respect to the early time points. Formulations T and U containing 8% polyisoprene (PIP) demonstrated a progressive deterioration in adhesion with time. In all cases, each formulation comparison that contained the larger percentage of XL10,000, also had less swelling of the matrix.

Example 2

Effect of Polymer Ratio on Drug Release

Figure 7:
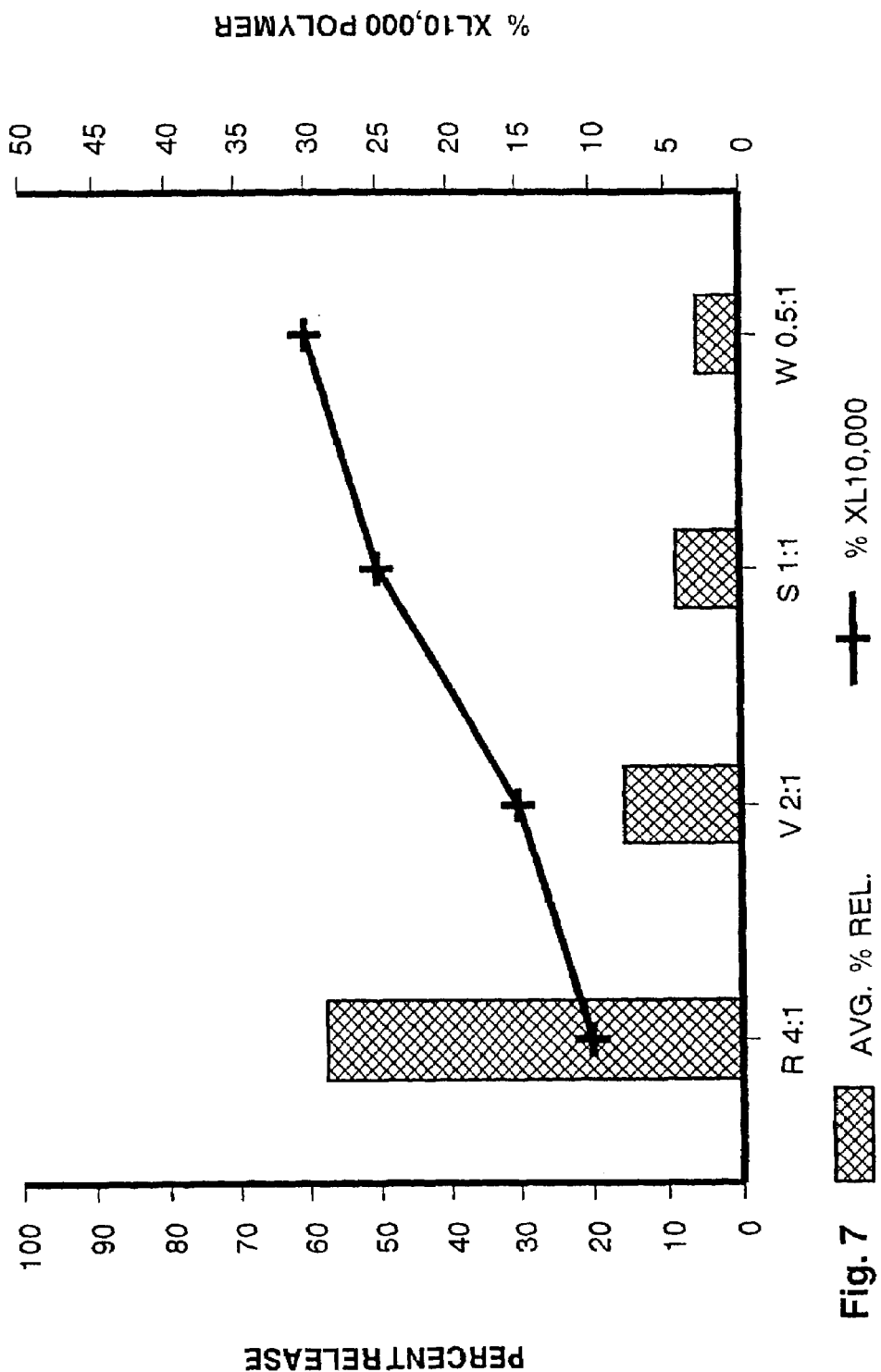
FIG. 7 is a graph illustrating the effect of polymer ratio on drug release of a transmucosal drug delivery system according to the invention.
Figure 8:
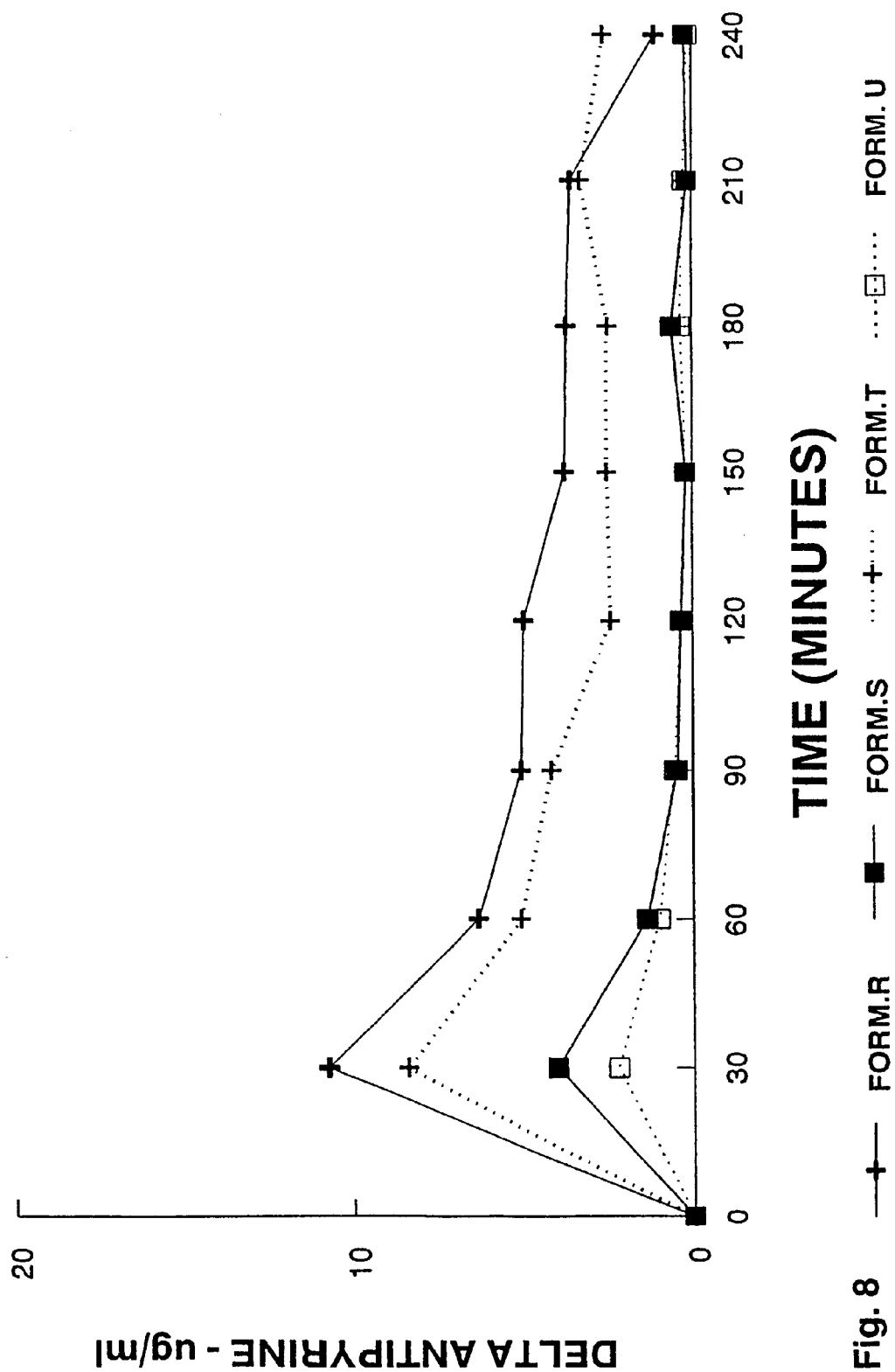
FIG. 8 is a graph illustrating in vitro drug release profile of a transmucosal drug delivery system.

The effect of controlling drug release by altering the ratio of crossed link polymer XL10,000 and polyisobutylene was assessed using antipyrene (MW=188.2) as the test drug molecule. Antipyrene was incorporated into the polymer matrix at 2% w/w. FIG. 7 shows that as the percentage of XL10,000 increases relative to PIB, the total amount of drug released at the end of four hours decreases. FIG. 8 illustrates a typical drug release profile seen with these formulations and also demonstrates that incorporating 8% w/w polyisoprene (PIP) did not significantly effect drug release from formulations T and U. Thus, R vs. T and S vs. U behave similarly in terms of drug release kinetics; but, formulations R and T do release more drug at all time points as compared to S and U.

As FIG. 5 illustrates, PIP did affect how the patch adhered to the gingival tissue over time. The preferred formulations for some applications are R, V, S, and W.

The results demonstrate that manipulation of the matrix composition can affect how the drug delivery system will behave in terms of membrane adhesion and swelling, and how the kinetics of drug release can be controlled. Thus, formulation R will be preferred where a high efflux of drug may be required. Formulation S can be used in those cases where a more sustained drug release would be warranted.

Example 3

Use of a Penetration Enhancer to Affect Therapeutic Response

The nonionic surfactant Lauricidin® was formulated into a TMDD of Examples 1 and 2 as a penetration enhancer (PE). Affect of Lauricidin® on systemic drug absorption was studied with the use of the drug medetomidine. Table 3 lists the individual components for four formulations in grams. Each formulation makes a net 50 gram lot of material.

TABLE 3

Formulations for Lauricidin ® TMD Patches

Formulation No.//Material in gms

| Material | I | II | III | IV |
|---|---|---|---|---|
| PIB | 16.0 | 14.0 | 16.6 | 16.0 |
| XL 10,000 | 4.0 | 3.5 | 4.2 | 4.0 |
| 971P | 27.5 | 27.5 | 27.5 | 27.7 |
| MED | 2.5 | 2.5 | 1.25 | 2.5 |
| LCN | 0.5 | 2.5 | 0.5 | 0.25 |

PIB, Polyisobutylene; XL 10,000, Polysar: 971P, Carbopol: MED, Medetomidine: LCN, Lauricidin ®.

Medetomidine is an alpha-2 agonist that acts within the central nervous system to produce pharmacological effects of sedation and analgesia. Hamline Robert L. et al., "Studies to Determine the Optimal Dose of Medetomidine," *Acta Vet. Scand.*, 85:89–95 (1989). 12 mm diameter patches of the formulations of Table 3 were stamped and attached to the gingival tissue of dogs. Electrocardiograms and observational scoring of sedation were recorded at specific time points post application of the patch.

Figure 9:
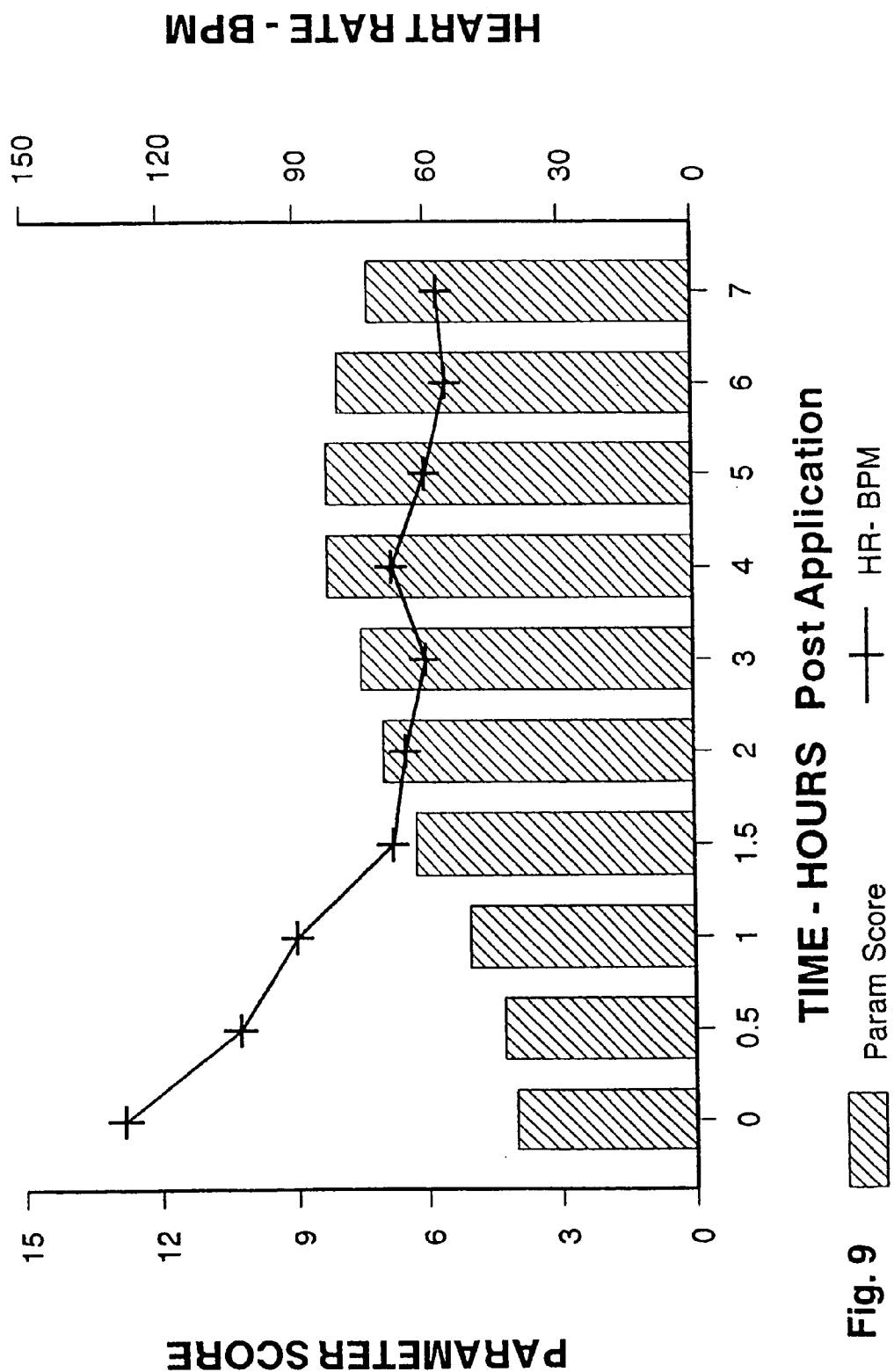
FIG. 9 is a graph illustrating the in vivo effect of a transmucosal drug delivery system including medetomidine without a penetration enhancer.

Alpha-2 agonists such as medetomidine produce A-V blockage in the heart which results in bradycardia. The canine heart is very sensitive to medetomidine and therefore a bradycardic response gives an early indication that drug is being released from the delivery system and accumulating systemically. FIG. 9 illustrates the bradycardic response when a 5% w/w medetomidine patch, without penetration enhancer, is applied to the upper gingival membrane of dogs (N=4), posterior to the canine tooth. As shown in FIG. 9, the bradycardic response occurs within 30 minutes of applying the TMDD patch to the gingival membrane indicating that drug is being quickly released from the device and absorbed through the mucosal membrane. The onset of sedation is slower since the therapeutic level of drug within the CNS must accumulate to an efficacious tissue concentration. Maximum sedation occurs at four hours post patch application at which time the bradycardic response is stabilizing. For certain applications such as sedation of an animal for transportation, this slow onset of action would not be a problem as induction of sedation is gentle and of long duration. However, for other applications, rapid onset is desirable for situations that may call for a short duration of sedation, but one that is more profound.

Figure 10:
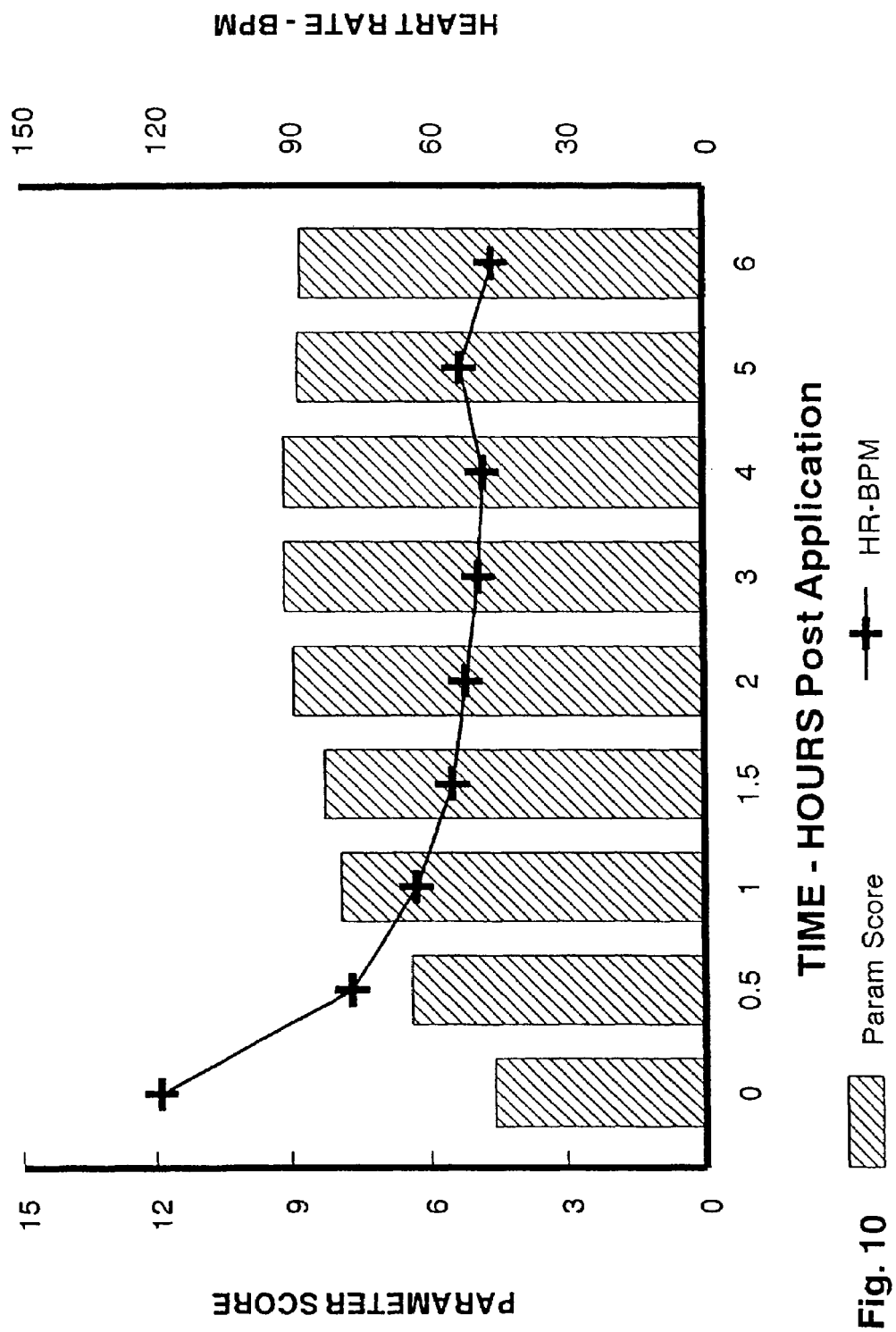
FIG. 10 is a graph illustrating the in vivo effect of a transmucosal drug delivery system including medetomidine with 1.0% w/w of the penetration enhancer glycerol monolaurate.

FIG. 10 illustrates the bradycardic response when a 5% w/w medetomidine patch, with 1.0% w/w Lauricidin®, is applied to the upper gingival membrane of dogs (N=7), posterior to the canine tooth. FIG. 10 illustrates that formulation I containing 1% w/w Lauricidin® shifts the drug response curves to the left. Without the PE (FIG. 9), a 47% decrease in heart rate had occurred by 1.5 hours post application. With the PE (FIG. 10), a thirty minute shift to the left occurs with a similar 47% decrease in heart rate at one hour. However, bradycardia is a non-threatening side effect of medetomidine and was not the pharmacological response of interest for this delivery system study. Sedation, in particular, and analgesia were the two modalities desired from this class of drug and delivery system study. FIG. 10 illustrates that for sedation of equivalent levels, there is an approximate decrease in time of onset of 2.5–3 hours. Thus, the PE allows drug leaving the TMDD to penetrate through the mucosal membrane more rapidly, achieving therapeutic levels in less time.

Formulation II (see Table 3) contained 5% w/w Lauricidin®. This patch formulation was extremely stiff after pressing into a sheet and did not have sufficient mucoadhesive properties to remain attached to the gingival membrane. Lauricidin® thus seems to have an upper limit at which it becomes incompatible with the formulation (stiffness and lack of adhesion).

Figure 11:
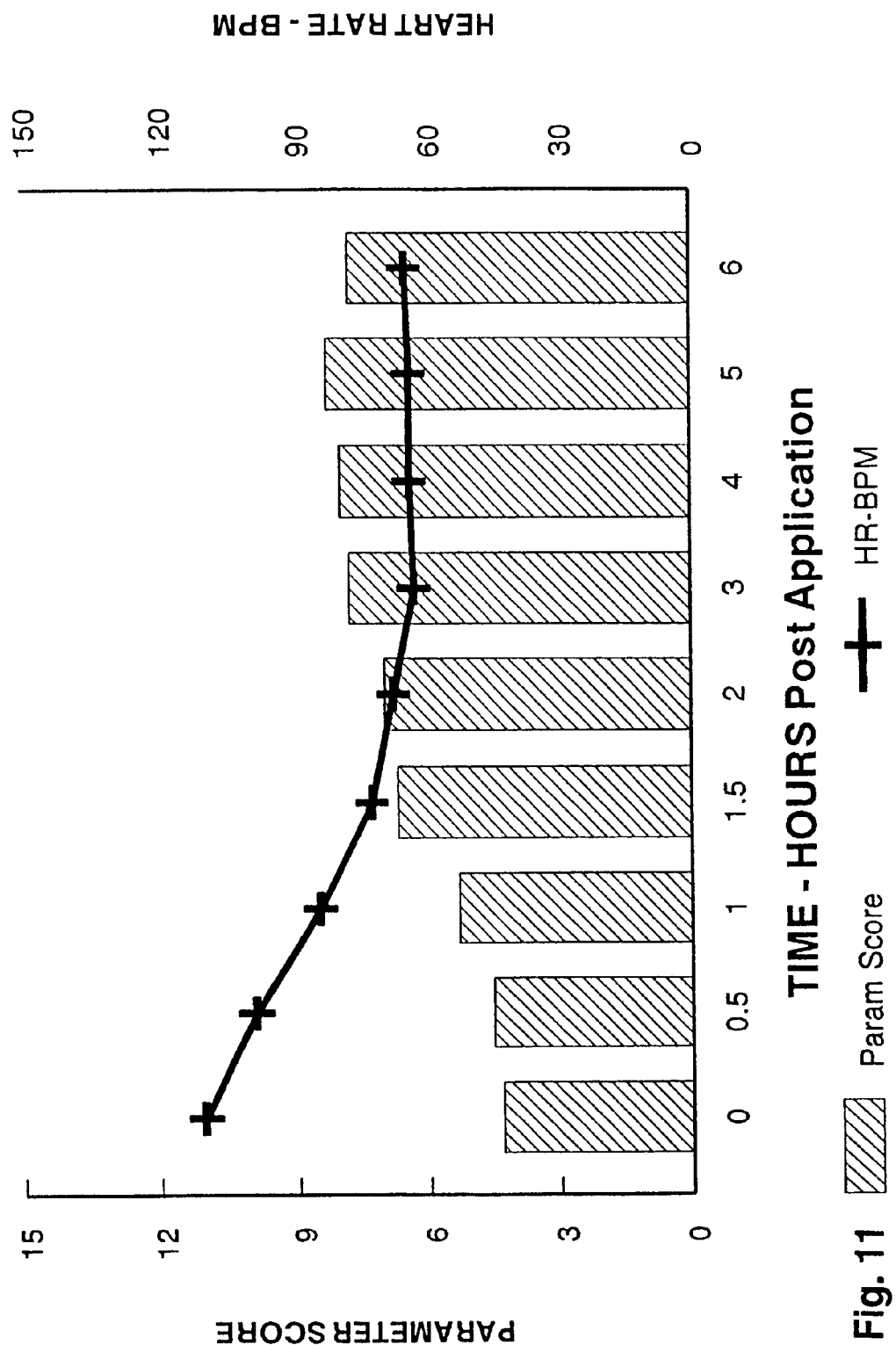
FIG. 11 is a graph illustrating the in vivo effect of a transmucosal drug delivery system including medetomidine with 0.5% w/w of the penetration enhancer glycerol monolaurate.

Formulation IV (see Table 3) contains 0.5% w/w Lauricidin®; medetomidine is maintained at a 5% load. The results of testing in the dog (N=4) are depicted in FIG. 11 and suggest that Lauricidin® also has a lower limit of concentration at which it no longer promotes transport of drug across mucosal membranes. The results show a right shift of the response curves, similar to that seen in FIG. 9 when no Lauricidin® is present in the patch formulation.

Figure 12:
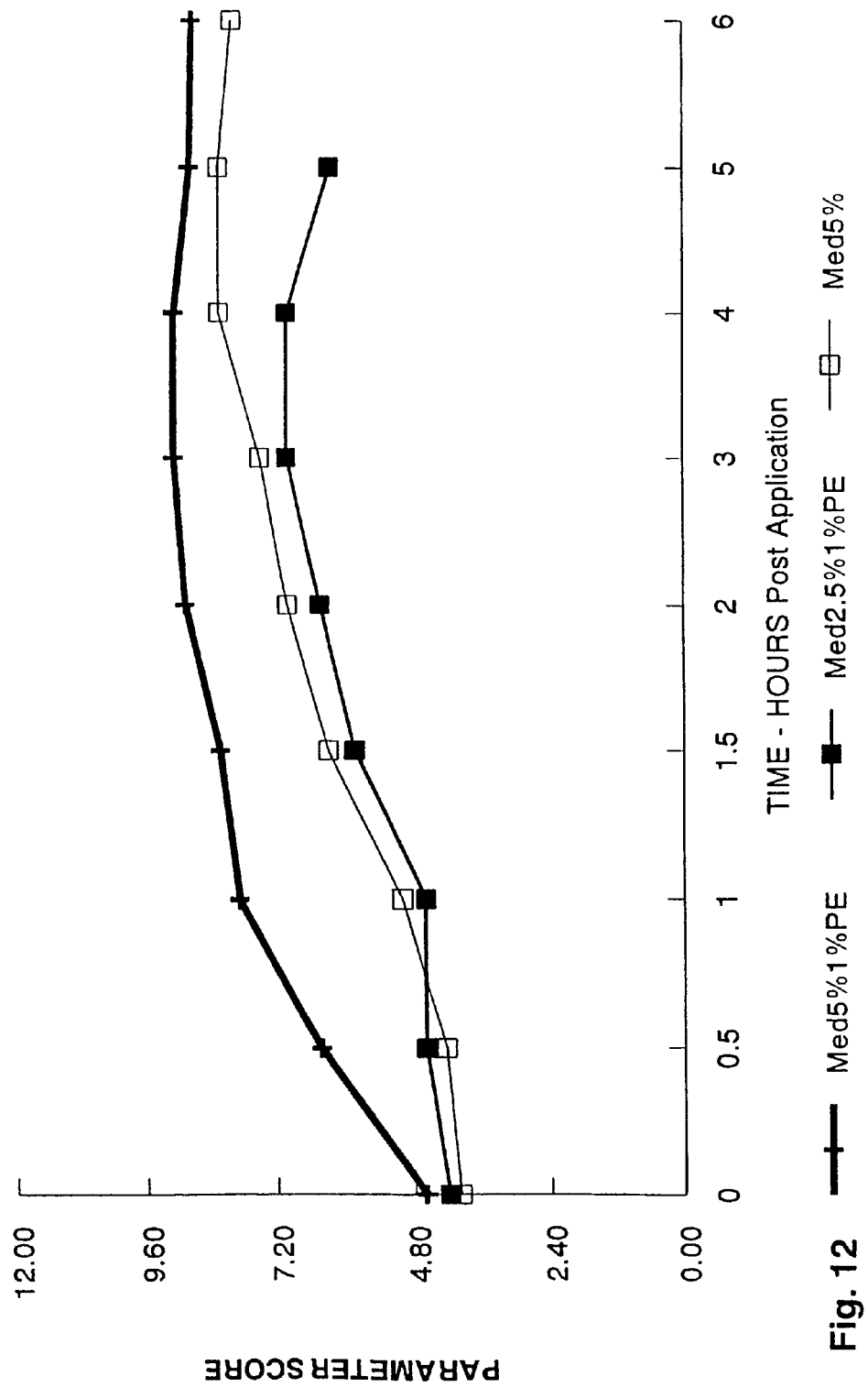
FIG. 12 is a graph illustrating enhancement of a dose of medetomidine with a penetration enhancer in dogs.

Lauricidin® may also enhance a drug response by allowing sufficient drug to quickly cross the mucosal membrane to elicit a pharmacological response that otherwise would not occur due to the barrier function of the oral membrane. Formulation III contains medetomidine at only 2.5% w/w with 1% w/w Lauricidin®. Normally, dogs will demonstrate very little sedation to medetomidine at 2.5% concentration in the patch. However, as FIG. 12 illustrates, 2.5% medetomidine with PE is just as effective as 5% w/w medetomidine without any PE. The sedation seems to be short lived as the parameter score is starting to return towards baseline values by 4–5 hours post application. Thus, the PE may be allowing an initial burst of drug to penetrate the gingival membrane which over time can not be sustained due to less drug being in the delivery system. This may be an approach to conserving drug while at the same time allowing for a patch configuration that will yield good sedation control but of short duration. FIG. 12 also illustrates the superior performance of the 5% medetomidine plus 1% PE patch over other formulations.

Thus, Lauricidin® can be an effective penetration enhancer, particularly for alpha-2 agonists. The time-response curve is shifted to the left and marginally effective doses may become efficacious due to increased permeability of the gingival mucosa. Further, no irritation or damage of the mucosal membrane was noted after six hours of wear suggesting that repetitive use of a patch containing Lauricidin® is safe.

Example 4

Preparation of a Unidirectional TMDD

From a TMDD formulation of Table 1, a unidirectional TMDD was prepared. In this example, the shape of the TMDD was circular. As discussed earlier, a TMDD of the invention need not be circular but can be any shape suitable for the particular application including oval, square, triangular, polygon, etc.

Figure 13:
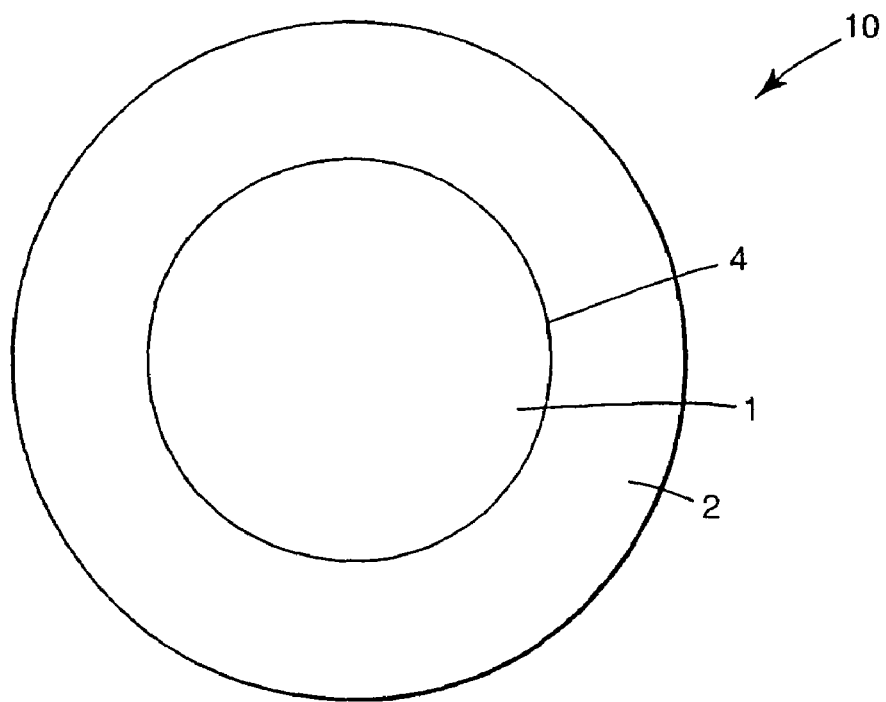
FIG. 13 is a top plan view of one embodiment of a unidirectional transmucosal drug delivery device according to the invention.
Figure 14:
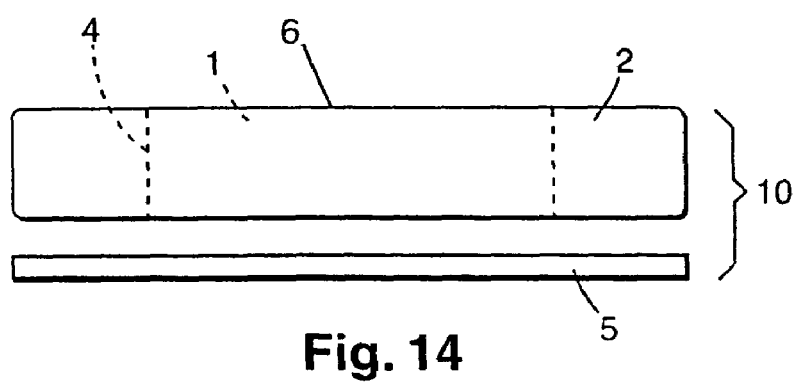
FIG. 14 is a profile view of the transmucosal drug delivery device of FIG. 13.

To prepare the TMDD a 20 mm diameter circular piece was punched from a placebo polymer formulation. Subsequently, a 12 mm diameter circular piece was punched and removed from the center of the 20 mm piece. This removed center piece was replaced with a 12 mm diameter punch taken from an identical polymer formulation which was formulated to include the drug antipyrene. FIG. 13 is a top plan view and FIG. 14 is a profile view of the resulting unidirectional TMDD 10. As illustrated, the center drug laden region 1 of the TMDD 10 is surrounded by an external drug free adhesive region 2. In the illustrated embodiment, the adhesive region 2 is a 4 mm thick ring of adhesive polymer surrounding the center region 1, thus sealing the lateral edge 4 of the drug laden region 1. The entire TMDD 10 was then covered with an impermeable membrane 5 which effectively sealed the patch on all sides except the top side 6 that would be in direct contact with the mucosal membrane. The impermeable membrane 5 was prepared from TEGADERM®.

Figure 15:
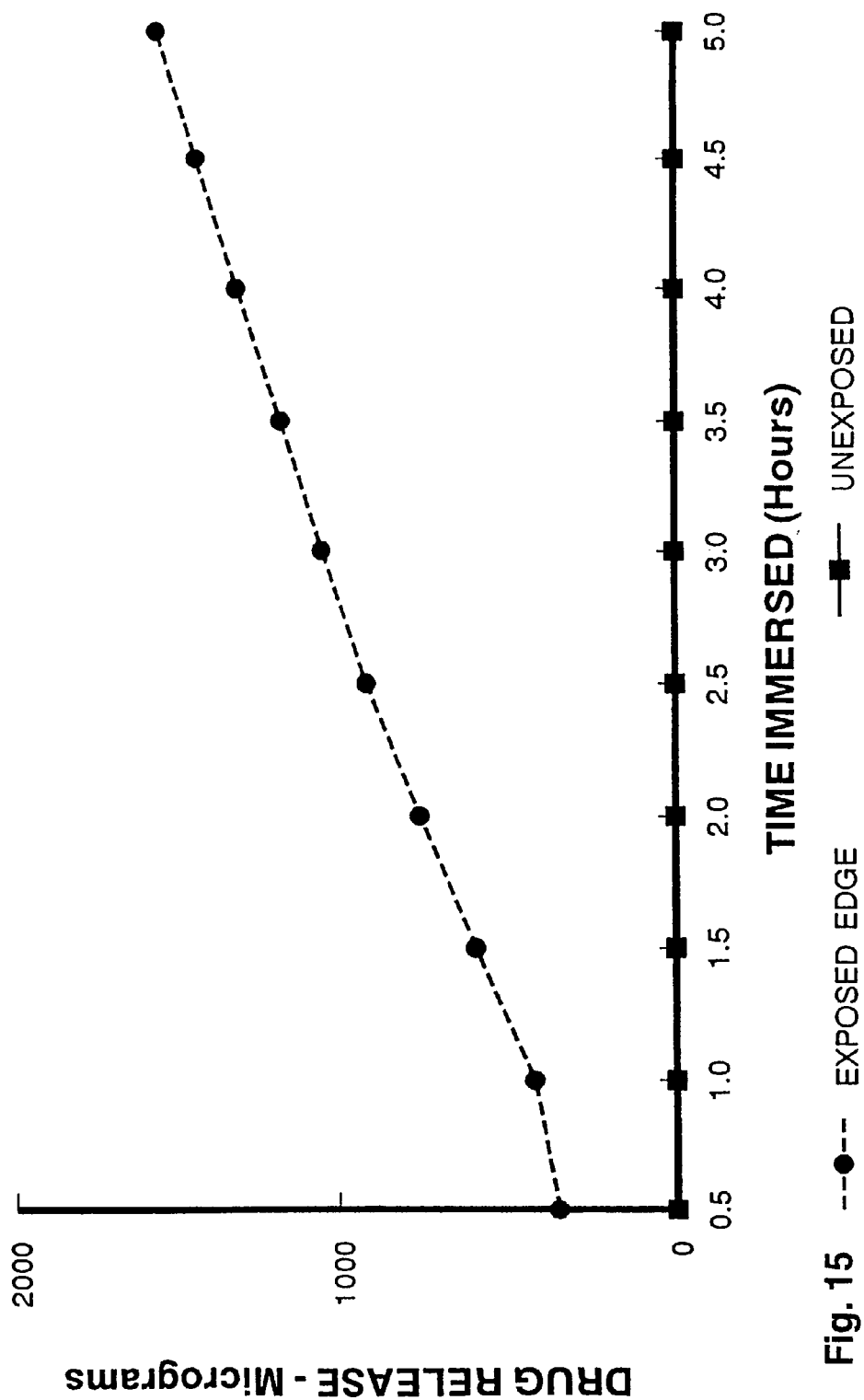
FIG. 15 is a graph illustrating in vitro drug release from a transmucosal drug delivery system having an exposed edge versus a delivery system having an unexposed edge.

FIG. 15 compares in-vitro drug release between two patches containing identical amounts of the drug antipyrene in which one has unprotected sides (exposed edge) while the other is ringed with a placebo polymer band (unexposed edge). Both patches were adhered to a glass slide and immersed in water for 5 hours. Drug could only escape from exposed edges of the TMDD. As illustrated, over the time course of five hours, a continuous leaching of drug from the TMDD having an exposed edge while the TMDD with the unexposed edge did not detectably leach any drug. Thus, by encasing the patch with both an impermeable backing film and outer polymer ring, it is possible to control unwanted leaching. This ensures that drug will only leave the drug delivery system from that portion of the patch adhering to the mucosal surface.

The herein disclosed center region polymer containing the drug can also be surrounded with other polymer formulations which may: (1) enhance adherence to the mucosal membrane, (2) control overall swelling of patch, (3) retard patch dissolution, and (4) improve overall performance of the patch delivery system. For example, the outer polymer layer may contain a high percentage of a cross-linked elastomer (e.g., XL-10,000) which would retard swelling. Also, the ratio of acrylic resin to elastomer may be adjusted to increase adhesion.

Allowing a small gap to exist between the outer perimeter of the center region and the inner perimeter of the outer adhesive region caused the outer region to curl backwards exposing the center region. This was eliminated when both perimeters were in contact with each other. Both the surface area of the center region and the width of the outer adhesive region can be varied to create an overall patch size that can be fitted to a selected site of attachment. The outer region can also be made of other polymers and design geometry which may have an advantage in improving adhesive strength and patch integrity.

The outer polymer region could also be used as a second drug reservoir which could contain drug(s) that might influence the drug in the center region. For instance, the outer region may contain a membrane permeation enhancer or a vasoconstrictive/vasodilator agent that would affect blood flow to the site of patch attachment. Both approaches would change the rate of drug absorption through the mucosal membrane and thus provide a means of controlling drug delivery.

Example 5

Cardiovascular and Sedative Effects of Different Patch Formulations

Table 4 lists additional TMDD formulations prepared with different ratios of dexmedetomidine, polyacrylic acid resins (carbopol 974P or 971P), polyisobutylene (PIB) (VISTANEX® LMMH), polyisoprene (PIP) (Natsyn® 2210 or Plioflex® 1027). Plioflex® 1027 is available from Goodyear Tire and Rubber Company.

As described in Example 1, using a conventional two roller mill, dexmedetomidine, polyacrylic acid, PIB and PIP were mixed and compressed to about 1.0 mm thick. Circular discs of about 0.5–0.8 cm$^2$ were punched from the compressed materials and backed and edged with a membrane, e.g., TEGADERM®.

Characteristics of patch hydration based on rate of water uptake was performed. Non-backed, non-edged patches were covered by a phosphate buffer at pH 2.6 for 24 hours and weight was plotted as function of time. The hydration ratio was calculated and expressed as a percent.

The drug release profile for the patches were determined using diffusion cells (Franz cell type). The patch was applied to a SPECTRA-POR® membrane. The test was performed at 37°±0.5° C. in a phosphate buffer at pH 7. The patch absorbed the aqueous medium via the membrane and released the drug through membrane in the receptor phase. The absorbence of dexmedetomidine was measured at 220 nm.

The cardiovascular and sedative effects of the patch formulations in Table 4 below are illustrated in FIGS. 16–19. The sedation score of FIGS. 18 and 19 comprised: normal=0; tired but standing=1; lying down, able to rise=2; lying down, rise with difficulty=3; and lying down unable to rise=4.

TABLE 4

Patch Formulation* - C974P or C971P

Figure 16:
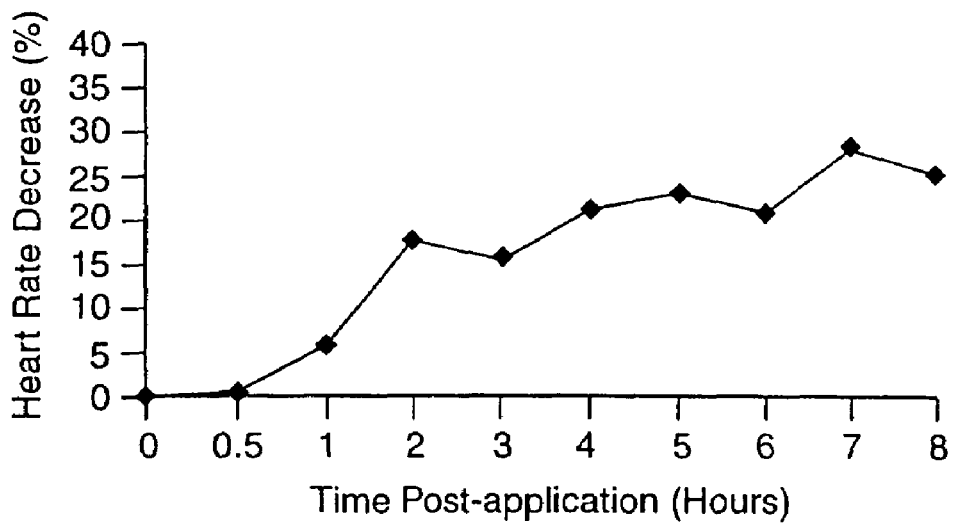
FIG. 16 is a graph illustrating the cardiovascular effect of patch formulation 1 of Table 4.
Figure 17:
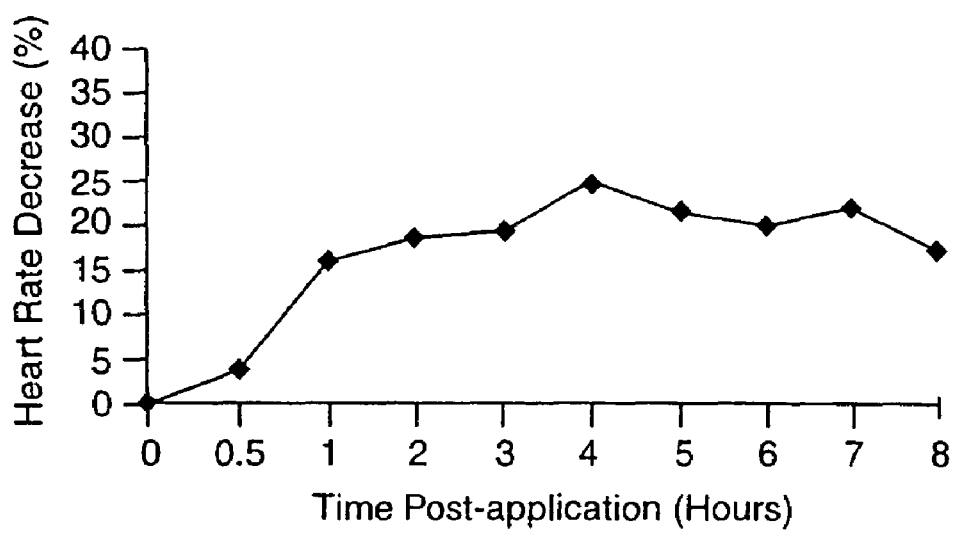
FIG. 17 is a graph illustrating the cardiovascular effect of patch formulation 2 of Table 4.
Figure 18:
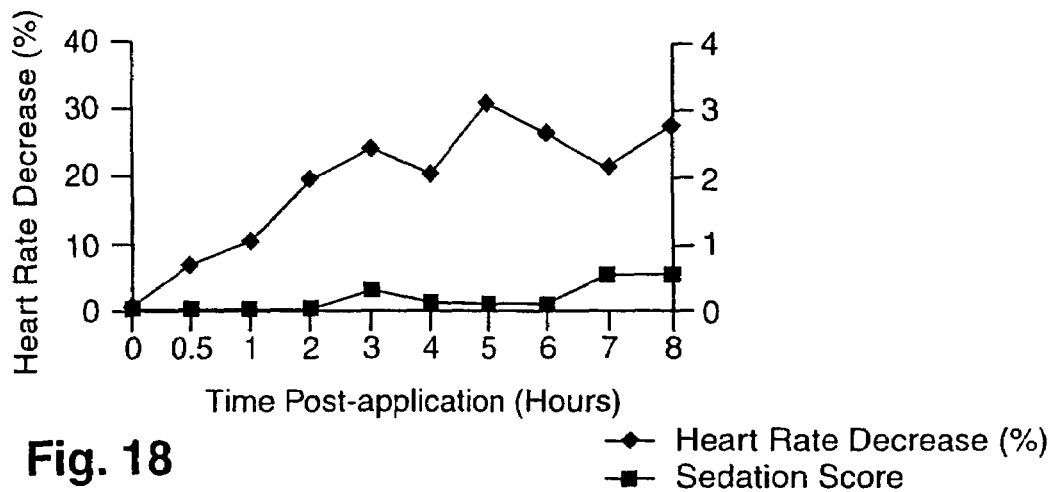
FIG. 18 is a graph illustrating the cardiovascular and sedative effects of patch formulation 3 of Table 4.
Figure 19:
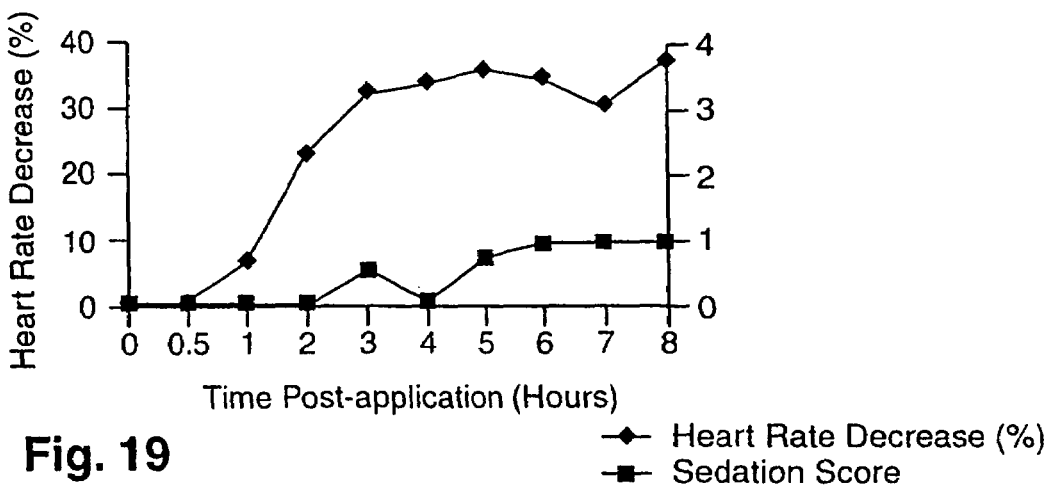
FIG. 19 is a graph illustrating the cardiovascular and sedative effects of patch formulation 4 of Table 4.

| FORMULATION ID | COMPONENTS | PERCENTAGE | EFFECT MEASURED/FIG. |
|---|---|---|---|
| 1 | PIB | 51 | Cardiovascular |
|  | PIP | 7 | FIG. 16 |
|  | C974P | 40 |  |
|  | Dexmedetomidine | 2 |  |
| 2 | PIB | 51 | Cardiovascular |
|  | PIP | 7 | FIG. 17 |
|  | C974P | 40 |  |
|  | Dexmedetomidine | 2 |  |
| 3 | PIB | 48 | Cardiovascular/ |
|  | PIP | 7 | Sedation |
|  | C974P | 40 | FIG. 18 |
|  | Dexmedetomidine | 5 |  |
| 4 | PIB | 48 | Cardiovascular/ |
|  | PIP | 7 | Sedation |
|  | CP71P | 40 | FIG. 19 |
|  | Dexmedetomidine | 5 |  |

* Patches 1 and 2 were about 0.8 cm$^2$ and patches 3 and 4 were about 0.5 cm$^2$. All patches were a matrix design that was backed and edged.

The invention provides new and unique systems and methods for administering a pharmaceutical agent to a non-human animal. The systems and methods disclosed herein are designed to address the unique physiological, anatomical, environmental and behavioral issues which are unique to non-human domestic animals. However, in some circumstances, it will be appreciated that the novel procedures disclosed can also be used for certain human conditions.

The above specification, examples and data provide a description of the manufacture and use of some presently preferred TMDD compositions suitable for the method of the invention. Since many embodiments of the invention are possible without departing from the spirit and scope of the invention, the invention resides in the claims hereinafter appended.

What is claimed is:

1. A transmucosal drug delivery device having a composition comprising:
   a polymeric resin;
   a linear elastomeric polymer;
   a cross-linked elastomeric polymer being 30–80% cross-linked; and
   a pharmacological agent,
   wherein the ratio of linear elastomeric polymer to cross-linked elastomeric polymer is about 1:2 to 5:1.

2. A transmucosal drug delivery device according to claim 1 wherein:
   (i) the polymeric resin is a particular polymeric resin present in an amount of from about 40 to about 65 percent by weight based on the total weight of the composition;
   (ii) the linear elastomeric polymer is present in an amount of from about 15 to about 50 percent by weight based on the total weight of the composition; and
   (iii) the cross-linked elastomeric poly is present in an amount of from about 5 to about 30 percent by weight based on the total weight of the composition.

3. The transmucosal drug delivery device according to claim 2 wherein the particulate polymeric resin is a linear polyacrylic acid resin.

4. The transmucosal drug delivery device according to claim 2 wherein the linear elastomeric polymer is selected from the group consisting of polyisobutylene, polyisoprene and mixtures thereof.

5. The transmucosal drug delivery device according to claim 2 wherein the cross-linked elastomeric polymer is a cross-linked butyl terpolymer rubber.

6. The transmucosal drug delivery device according to claim 2 further comprising a penetration enhancer.

7. The transmucosal drug delivery device according to claim 1 wherein the pharmacological agent is selected from the group consisting of detomidine, medetomidine, dexmedetomidine, atapamazole, fentanyl, ketamine and pharmaceutically acceptably salts thereof.

8. The transmucosal drug delivery device according to claim 6 wherein the pharmacological agent is present in an amount of from about 2 to about 5 percent by weight based on the total weight of the composition and the pharmacological agent is selected from the group consisting of medetomidine, dexmedetomidine and pharmaceutically acceptable salts thereof; and glycerol monolaurate is present in an amount of from about 0.5 to 5 percent by weight based on the total weight of the composition.

9. The transmucosal drug delivery device according to claim 1 wherein the pharmacological agent is present in an amount from about 0.5 to about 10 percent based on the total weight of the composition.

* * * * *